United States Patent
Teff et al.

(10) Patent No.: US 7,883,639 B2
(45) Date of Patent: Feb. 8, 2011

(54) ADDITIVES TO PREVENT DEGRADATION OF CYCLIC ALKENE DERIVATIVES

(75) Inventors: Daniel J. Teff, Chandler, AZ (US); John L. Chagolla, Mesa, AZ (US)

(73) Assignee: Fujifilm Electronic Materials, U.S.A., Inc., North Kingstown, RI (US)

( * ) Notice: Subject to any disclaimer, the term of this patent is extended or adjusted under 35 U.S.C. 154(b) by 891 days.

(21) Appl. No.: 11/519,524

(22) Filed: Sep. 12, 2006

(65) Prior Publication Data

US 2007/0057234 A1 Mar. 15, 2007

Related U.S. Application Data

(60) Provisional application No. 60/716,283, filed on Sep. 12, 2005.

(51) Int. Cl.
C09K 15/08 (2006.01)
C10L 1/183 (2006.01)
C23C 16/00 (2006.01)
H01L 21/00 (2006.01)

(52) U.S. Cl. .................... 252/182.29; 252/404; 44/312; 44/442; 44/443; 44/445; 427/255.6; 438/758; 438/778

(58) Field of Classification Search .................. 44/312, 44/442, 443, 445; 252/182.29
See application file for complete search history.

(56) References Cited

U.S. PATENT DOCUMENTS

| | | | |
|---|---|---|---|
| 2,964,575 A | 12/1960 | Schul et al. | |
| 2,969,399 A * | 1/1961 | Schmerling | 568/585 |
| 4,066,562 A | 1/1978 | Wollensak et al. | |
| 4,222,884 A | 9/1980 | Malec | |
| 4,246,367 A | 1/1981 | Curtis, Jr. | |
| 4,278,554 A | 7/1981 | Malec | |
| 4,362,848 A | 12/1982 | Friedli et al. | |
| 4,503,267 A * | 3/1985 | Pavlin | 568/753 |
| 4,551,489 A * | 11/1985 | Bayha | 523/501 |

(Continued)

FOREIGN PATENT DOCUMENTS

JP 63174939 A 7/1988

OTHER PUBLICATIONS

Extended Search Report issued on Dec. 1, 2009 in European Application No. 06803326.5.

(Continued)

*Primary Examiner*—Joseph D Anthony
(74) *Attorney, Agent, or Firm*—Fish & Richardson P.C.

(57) ABSTRACT

A stabilized cyclic alkene composition comprising one or more cyclic alkenes, and at least one antioxidant compound having the formula (I),

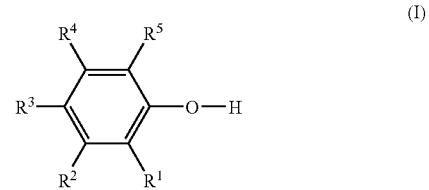

wherein $R^1$ through $R^5$ can each independently be H, OH, $C_1$-$C_8$ linear, branched, or cyclic alkyl, $C_1$-$C_8$ linear, branched, or cyclic alkoxy or substituted or unsubstituted aryl, and wherein the antioxidant compound is present in an amount between 1 ppm and 200 ppm, and wherein said composition is purged with at least one inert gas after said composition is introduced to a container intended for storage or shipping of said composition. A method for forming a layer of carbon-doped silicon oxide on a substrate, which uses the stabilized alkene composition and a silicon containing compound.

40 Claims, 1 Drawing Sheet

U.S. PATENT DOCUMENTS

| | | | |
|---|---|---|---|
| 4,744,881 A | | 5/1988 | Reid |
| 4,745,141 A | * | 5/1988 | Akiyama et al. ............ 523/500 |
| 4,979,545 A | | 12/1990 | Fair |
| 5,091,594 A | * | 2/1992 | Kupper et al. ................ 568/789 |
| 5,279,338 A | | 1/1994 | Goossens |
| 5,359,023 A | | 10/1994 | Wang et al. |
| 5,451,260 A | | 9/1995 | Versteeg et al. |
| 5,536,323 A | | 7/1996 | Kirlin et al. |
| 5,551,309 A | | 9/1996 | Goossens et al. |
| 5,607,002 A | | 3/1997 | Siegele et al. |
| 5,679,631 A | * | 10/1997 | Bohnert et al. .............. 510/411 |
| 5,835,678 A | | 11/1998 | Li et al. |
| 5,882,416 A | | 3/1999 | Van Buskirk et al. |
| 5,973,085 A | | 10/1999 | Muhlebach et al. |
| 5,992,830 A | | 11/1999 | Daubs et al. |
| 6,040,388 A | | 3/2000 | Nishimura et al. |
| 6,063,893 A | * | 5/2000 | Karasawa et al. ............. 528/93 |
| 6,159,871 A | | 12/2000 | Loboda |
| 6,265,490 B1 | | 7/2001 | Morel-Fourrier et al. |
| 6,271,658 B1 | | 8/2001 | Vallinan et al. |
| 6,312,793 B1 | | 11/2001 | Grill et al. |
| 6,383,555 B1 | | 5/2002 | Hayash et al. |
| 6,437,443 B1 | | 8/2002 | Grill et al. |
| 6,479,110 B2 | | 11/2002 | Grill et al. |
| 6,541,398 B2 | | 4/2003 | Grill et al. |
| 6,583,048 B1 | | 6/2003 | Vincent et al. |
| 6,596,627 B2 | | 7/2003 | Mandal |
| 6,604,492 B2 | | 8/2003 | Porter et al. |
| 6,633,076 B2 | | 10/2003 | Krishnaraj et al. |
| 6,756,323 B2 | | 6/2004 | Grill et al. |
| 6,815,373 B2 | | 11/2004 | Singh et al. |
| 6,846,515 B2 | | 1/2005 | Vrtis et al. |
| 6,858,697 B2 | | 2/2005 | Mayorga et al. |
| 6,914,335 B2 | | 7/2005 | Andideh et al. |
| 7,101,948 B2 | | 9/2006 | Mayorga et al. |
| 7,108,771 B2 | | 9/2006 | Xu et al. |
| 7,129,311 B2 | | 10/2006 | Teff et al. |
| 7,531,590 B2 | | 5/2009 | Teff et al. |
| 2002/0037958 A1 | | 3/2002 | Benage et al. |
| 2003/0220422 A1 | * | 11/2003 | Kaprinidis ................... 524/86 |
| 2004/0116565 A1 | * | 6/2004 | Kaprinidis et al. .......... 524/247 |
| 2004/0127070 A1 | * | 7/2004 | Teff et al. .................... 438/787 |
| 2004/0198922 A1 | * | 10/2004 | Adegawa .................... 525/390 |
| 2005/0131182 A1 | | 6/2005 | Murakami et al. |
| 2006/0009372 A1 | * | 1/2006 | Mansfeld et al. .............. 512/8 |
| 2006/0270787 A1 | | 11/2006 | Teff et al. |
| 2009/0159843 A1 | | 6/2009 | Mayorga et al. |
| 2009/0159844 A1 | | 6/2009 | Mayorga et al. |

OTHER PUBLICATIONS

Extended Search Report issued on Dec. 1, 2009 in European Application No. 06803374.5.
International Search Report dated Apr. 23, 2007 for PCT/US06/35303.
Matheson Tri-Gas, Inc., "Material Safety Data Sheet", Jun. 14, 2007, Basking Ridge, NJ.
Styrene Producers Association, CEFIC Sector Group, "Styrene Monomer: Environmental, Health, Safety Transport and Storage guidelines," Mar. 3, 2008, Belgium.
L. Ross C. Barclay and Melinda R. Vinqvist, "Phenols as antioxidants," *The Chemistry of Phenols*. Edited by Z. Rappoport, 2003 John Wiley & Sons, Ltd., Hoboken, NJ.
European Search Report Apr. 18, 2006.
Clariant LSM 171779, Norbornadiene Data Sheet, created on Dec. 12, 2003 and modified on Aug. 24, 2006.
Clariant Norbornadiene Material Specification, Sep. 5, 2006.
Aldrich B33803 Bicyclo[2.2.1]hepta-2,5-diene Specification Sheet, 2009.
Aldrich Bicyclo[2.2.1]hepta-2,5-diene Specification Sheet, 2009.
B. S. Bjola, et al., "Molar Excess Volumes and Molar Excess Enthalpies of Binary Liquid Mixtures of Norbornadiene + Benzene, + Cyclohexane, + Decane, and + Carbon Tetrachloride", J. Chem. Eng. Data 2002, 47, 250-253.
Online chemical jounal "LOOKCHEM" (www.lookchem.com/cas-128/128-37-.html), for Butylated hydroxytoluene, online chemical journal accessed on Aug. 16, 2010.

* cited by examiner

ADDITIVES TO PREVENT DEGRADATION OF CYCLIC ALKENE DERIVATIVES

CROSS REFERENCE TO RELATED APPLICATION

The present application claims priority of U.S. Provisional Application Ser. No. 60/716,283, filed on Sep. 12, 2005.

BACKGROUND OF THE INVENTION

1. Field of the Invention

The present disclosure relates generally to cyclic alkene compositions that exhibit stability during extended storage. More particularly, the present disclosure is directed to cyclic alkene derivatives stabilized with one or more antioxidant compounds and a purge method to reduce or eliminate residue formation during storage of such compositions, and methods for use of such compositions to form dielectric films.

2. Background of the Invention

The semiconductor industry requires numerous types of thin and thick films to prepare semiconductor devices, many of which are based on silicon. The elemental composition of these films is typically some combination of silicon and carbon with various combinations of oxygen, hydrogen, and fluorine. In U.S. Pat. No. 6,914,335, Andideh et al. teach how layers can differ and can be used for different purposes, while in U.S. Pat. No. 6,846,515, Vrtis et al. teach ranges of silicon, oxygen, carbon and hydrogen for dielectric films preferred by the semiconductor industry. A frequently used process is chemical vapor deposition, and there are numerous variations of this process.

In a typical chemical vapor deposition process, a silicon containing compound is introduced into a deposition chamber containing a substrate to be coated. The silicon containing compound is then chemically or physically altered (i.e., reacted with another component, or subjected to application of an energy source such as radiation, heat (thermal CVD), or plasma (PECVD), etc.) to deposit a film on the substrate. Deposited films containing only silicon and oxygen (i.e., silicon oxide) have a dielectric constant of approximately 4 in the absence of pores, while films that also contain carbon (i.e., carbon doped silicon oxide) and/or pores often have dielectric constants lower than 4. Films with a dielectric constant below about 2.7 are preferred for newer semiconductor devices. In U.S. Pat. No. 6,583,048, Vincent et al. provide examples of chemical vapor deposition techniques, dielectric constants, and examples of films that are desirable in the semiconductor industry.

The properties of a layer deposited on a substrate, such as dielectric constant, film hardness and refractive index, are influenced by changing the composition of the chemistry that is fed into the film deposition tool and the process employed. The film properties can be tuned by changing the identity of the silicon containing compound by using a different flow gas, by using one or more different reactive gases, or by using post-deposition anneal techniques. Another means to affect the layer properties is to use a combination of silicon containing compounds or to combine a silicon containing compound(s) with one or more additive compounds. These techniques can be employed to alter the chemical composition of the film to adjust the film to the desired properties. U.S. Pat. Nos. 6,633,076, 6,2176,58, 6,159,871, 6,479,110 and 6,756,323, herein incorporated by reference, give examples of how film properties are affected by changing deposition parameters or component mixtures.

An alternative method of use for the additive compound is to employ compounds whose fragments or atoms are only temporarily resident in the film. The film can be post-treated to drive the fragments or atoms out of the film using radiation or a combination of radiation and reactive gases, such as oxygen, to create voids in the resulting film. This approach affects the properties (e.g. dielectric constant) of the deposited film. The compounds employed in this manner are described as porogens.

Typical porogens used in this type of approach are predominately composed of carbon and hydrogen. Examples of some of the classes of cyclic alkene compounds of interest as porogens are described in U.S. Pat. Nos. 6,846,515 and 6,756,323.

High volume semiconductor manufacturing places stringent demands on the equipment and on the purity and stability of the chemistries that flow through the equipment. Even trace amounts of some contaminants can degrade the properties of a deposited film. A chemical that is sent through chemical lines and a vaporizer means is expected to transport and vaporize cleanly and leave behind little or no residue during extended use. The longer a piece of equipment can operate between scheduled or unscheduled maintenance periods (such as, to clean out chemical lines or a vaporizer means that is fouled or clogged with polymeric residue), the more productive the tool is, making it more cost-effective. A deposition tool that must be shut down often for cleaning and maintenance is not as appealing to semiconductor manufacturing customers. Thus, continuous, long term operation of equipment is desirable. Vaporizer means can include several types of vaporization apparatuses, including, but not limited to, heated vaporizers (see U.S. Pat. Nos. 6,604,492, 5,882,416, 5,835,678, and references therein), bubbler ampoules (see U.S. Pat. Nos. 4,979,545, 5,279,338, 5,551,309, 5,607,002, 5,992,830 and references therein), flash evaporators (see U.S. Pat. No. 5,536,323 and references therein) and misting apparatuses (see U.S. Pat. Nos. 5,451,260, 5,372,754, 6,383,555, and references therein).

These purity and stability requirements are often difficult to achieve. Many materials may oxidize or polymerize to some degree. Even small amounts of such byproducts may be undesirable for many semiconductor applications.

1,3,5,7-Tetramethylcyclotetrasiloxane (TMCTS) is a representative silicon containing compound which can be employed to produce low k dielectric films and is an example of the difficulty in maintaining stability. Initial work to establish reliable manufacturing processes was hampered by the product gelling at different points in the deposition process, including the chemical lines, vapor delivery lines, and within the deposition chamber. This indicated that the stability of pure TMCTS was not sufficient, and a variety of additives were studied by Teff et al. in United States Patent Application Publication No. 2004/0127070. It was found that antioxidants were highly effective to stabilize TMCTS against exposure to air, specifically oxygen, for extended periods of time at ambient or elevated temperatures. When antioxidant-stabilized TMCTS is used now in semiconductor manufacturing, processes are more stable, and gel formation in a deposition tool is reduced significantly.

Norbornadiene (NBDE) is an example of a cyclic diene of interest for use as a porogen primarily due to the bond strain in its structure and its tendency to undergo thermal reactions to form volatile materials when heated (see U.S. Pat. Nos. 6,846,515, 6,479,110, 6,437,443, and 6,312,793). NBDE and similar cyclic alkene derivatives can react with oxygen to either polymerize or oxidize, forming higher molecular weight, lower volatility materials which may or may not be soluble in the cyclic alkene monomer. This reaction can cause significant degradation of the cyclic alkene over time, even after brief air exposure at room temperature.

NBDE forms highly soluble, low volatility solid products in the presence of adventitious air, which is not readily apparent on visual inspection before the NDBE is evaporated. This can result in accumulation of the solid product in a vaporizer means as the volatile NBDE is evaporated away. If the surface area of the vaporizer means is small, it is possible that small amounts of residue can hinder the evaporation of NBDE, eventually causing the vaporizer means to clog with the low volatility solids. If a bubbler ampoule is employed as the vaporizer means, oxidation products could initiate a polymerization process, causing the entire contents of the bubbler to polymerize and block the flow gas inlet line. This is especially true with bubblers that are constantly heated to assist the vaporization process. Once a vaporizer means becomes plugged with solid, the only remedy is to disassemble and clean or replace the affected vaporizer means, which is very costly and time consuming. Safety issues are also a concern if pressurized chemical lines and valves become blocked with the low volatility solid.

The semiconductor industry requires stable, predictable and reliable products, and this behavior is unacceptable for high volume semiconductor manufacturing. Therefore, it is necessary to find a means to stabilize NBDE to ensure that the product does not easily decompose during transport from the chemical supplier to the end-use process, even after exposure to various conditions. However, chemistry of the cyclic alkene compounds differs considerably from the chemistry of the silicon containing compounds typically employed, so it is not obvious that the same compounds that stabilize the silicon containing compounds will stabilize the cyclic alkene compounds.

TMCTS is believed to ring open and polymerize in the presence of oxygen. Further, TMCTS has Si—H bonds that are reactive with molecular oxygen (see U.S. Patent Application Publication No. 2004/0127070 and U.S. Pat. No. 6,858,697). By contrast, NBDE will slowly oligomerize in the presence of air, but it will not gel and the ring structure remains intact during the oligomerization process. Where TMCTS can completely polymerize as a gel inside a chemical line upon exposure to air, NBDE instead forms a highly soluble, medium to high molecular weight and low volatility oligomer that is not apparent upon visual inspection, or easily detectable by gas chromatography (GC). Instead, the resulting oligomers are detected when the volatile NBDE is evaporated away to leave behind the low volatility oligomers.

NBDE and similar materials are sometimes stabilized with antioxidants, such as butylated hydroxytoluene, also known as 2,6-di-tert-butyl-4-methylphenol (BHT), (see Clariant LSM 171779 Norbornadiene Specification Sheet and Aldrich Catalog Number B3,380-3). These antioxidants are commonly added at concentrations of 0.02 to 0.25 wt % (200 to 2,500 ppm), but additives can exceed this amount when the manufacturer wants to increase shelf life. Chemical manufacturers prefer to use BHT due to its low cost and availability. However, the concentrations of these additives are higher than desired for semiconductor purposes, because high concentrations of antioxidants will adversely affect the purity of the porogen composition. These higher concentrations will also leave behind greater amounts of residue on the vaporization equipment, which adds to the cleaning and maintenance costs associated with the chemical vapor deposition process.

An alternate method for stabilizing silicon containing compounds has been described. In U.S. Pat. No. 5,556,999, Yamada et al. demonstrate that using $CO_2$ or $SO_2$ to purge silicon containing compounds, such as methyldiethoxysilane, prevents decomposition of the compounds during storage. Yamada et al. do not teach the exact mechanism by which $CO_2$ or $SO_2$ stabilize such compounds, and it is not obvious that the method will work for stabilizing cyclic alkenes for depositing semiconductor films. While $CO_2$ is compatible with processes to form dielectric films, the sulfur content in $SO_2$ is not compatible with such processes. Further, $SO_2$ is not expected to be compatible with cyclic alkenes due to its propensity to form acid in the presence of trace moisture, where acid can initiate cyclic alkene polymerization.

Thus the prior art does not describe a phenolic additive and inert gas container purge method which can stabilize cyclic alkenes from oligomerization or other undesired reactions during storage.

SUMMARY OF THE INVENTION

The present disclosure provides a stabilized cyclic alkene composition comprising:
  a) one or more substituted or unsubstituted cyclic alkenes, and
  b) an antioxidant composition comprising at least one compound of Formula (I), wherein the antioxidant composition is present in a concentration between 1 ppm and 200 ppm, and wherein $R^1$ through $R^5$ can each independently be H, OH, $C_1$-$C_8$ linear, branched, or cyclic alkyl, $C_1$-$C_8$ linear, branched, or cyclic alkoxy or substituted or unsubstituted aryl,
  wherein said composition is purged with at least one inert gas comprising a gas selected from the group consisting of helium, neon, argon, krypton, xenon, radon, nitrogen, carbon monoxide or carbon dioxide, after said composition is introduced to a container intended for storage or shipping of said composition.

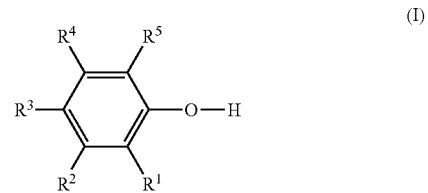

The present disclosure further provides a process using a cyclic alkene composition for forming a layer of carbon-doped silicon oxide on a wafer. The process comprises the steps of:
  a) providing a cyclic alkene composition in a container, a silicon containing compound in a container, a film deposition tool, a film deposition chamber within said film deposition tool, a means for connecting the containers to the film deposition chamber within said film deposition tool, a stream of carrier gas to sweep the cyclic alkene composition and the silicon containing compound through the connecting means into the film deposition chamber, and a substrate within the film deposition chamber of the film deposition tool;
  b) introducing the vapors of the cyclic alkene composition and the silicon containing compound into the carrier gas stream;
  c) transporting the vapor of the cyclic alkene composition and silicon containing compound into the film deposition chamber; and d) using one or more energy means, to form a carbon doped silicon oxide film on the substrate, wherein said cyclic alkene composition comprises:
1) one or more substituted or unsubstituted cyclic alkenes, and
2) an antioxidant composition comprising at least one compound of Formula (I), wherein the antioxidant composition is present in a concentration between 1 ppm and 200 ppm, and wherein $R^1$ through $R^5$ can each independently be H, OH, $C_1$-$C_8$ linear, branched, or cyclic alkyl, $C_1$-$C_8$ linear, branched, or cyclic alkoxy or substituted or unsubstituted aryl, wherein said cyclic composition is purged with at least one inert gas comprising a gas selected from the group consisting of helium, neon, argon, krypton, xenon, radon, nitrogen, carbon monoxide or carbon dioxide, after said composition is introduced to a container intended for storage or shipping of said composition.

DETAILED DESCRIPTION OF THE INVENTION

Figure 1:
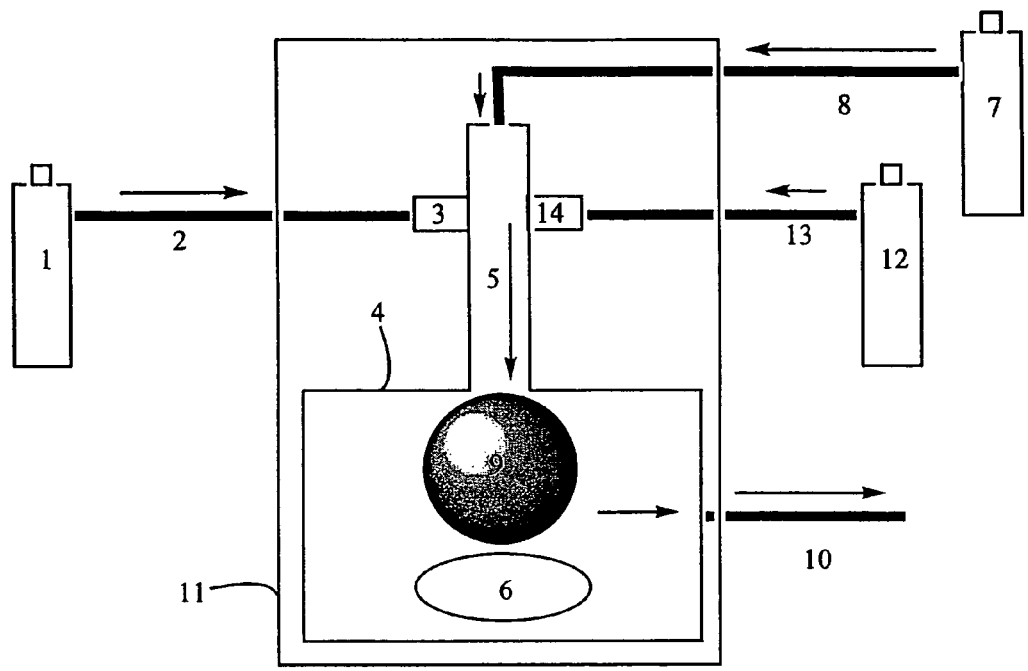
FIG. 1 is a representation of a film deposition tool used in the semiconductor industry for use with the compositions according to the present disclosure, where two independent vaporizer means are used with two separate precursors.

The semiconductor industry requires numerous types of thin and thick films to prepare semiconductor devices. A frequently used process to prepare these films is chemical vapor deposition and there are numerous variations of this process. In a typical chemical vapor deposition process, a silicon containing compound is introduced into a deposition chamber containing the substrate to be coated. The silicon containing compound is then chemically or physically altered (reacted with another component, or subjected to application of an energy source such as radiation, heat (thermal CVD), or plasma (PECVD), etc.) to deposit the film on the substrate.

High volume semiconductor manufacturing places stringent demands on the film deposition equipment and on the purity and stability of the chemistries that flow through the equipment. Even trace amounts of some contaminants can degrade the properties of a deposited film. A chemical that is sent through chemical lines and a vaporizer means is expected to transport and vaporize cleanly and leave behind little or no residue during extended use. The longer a piece of equipment can operate between scheduled or unscheduled maintenance periods (such as, to clean out chemical lines or a vaporizer means that is fouled or clogged with polymeric residue), the more productive the tool is, making it more cost-effective. A deposition tool that must be shut down often for cleaning and maintenance is not as appealing to semiconductor manufacturing customers. Thus, continuous, long term operation of equipment is desirable.

These purity and stability requirements are often difficult to achieve. Many materials may oxidize, polymerize or rearrange to some degree. Even small amounts of such byproducts may be undesirable for many semiconductor applications. Thus materials used in the semiconductor industry may require additives and purging methods to prevent formation of undesired side reactions before reaching a deposition chamber.

Cyclic alkenes are materials of interest for chemical vapor deposition to form low k dielectric films in the semiconductor industry that require additives to be stabilized.

Chemicals, including additives, that are useful for the semiconductor industry are typically limited to species that have a boiling point lower than 300° C. Furthermore, the specific application in the semiconductor industry may dictate additional properties that the precursor must have. For example, formation of interlayer dielectric (ILD) films restricts precursor selection to use only silicon, oxygen, carbon and hydrogen due to compatibility issues with the surrounding layers in a chip. The selection of radical inhibitors and purge gases must also follow this basis, so nitrogen, sulfur and phosphorous that are found in common radical inhibitors and antioxidants such as lecithin and lipoic acid must be avoided.

In addition to stabilizing the cyclic alkenes, it is advantageous to minimize the boiling point difference between the cyclic alkenes and the stabilizer that is used. For example, NBDE boils at 89° C. while BHT boils at 265° C. This difference is enough to cause significant problems in a semiconductor deposition tool vaporizer means having a small vaporization chamber.

Commonly, these vaporizer means are set at the lowest possible temperature to allow complete vaporization of a liquid product while avoiding thermal decomposition. It is also necessary to balance thermal loading of the vaporizer means to correctly vaporize the product without saturating a vapor stream. With these considerations, it is a fine balance to vaporize the source chemical without adding too much heat. Thus, it is most often the case that higher molecular weight components are poorly vaporized, or not vaporized at all, and these tend to accumulate in the vaporizer means to eventually clog it. For this reason, it is desirable to reduce the difference between the boiling points of cyclic alkene derivatives and their stabilizers, and to reduce the concentrations of the stabilizers to their lowest levels. It is not obvious, however, which higher volatility additives with a desirable elemental composition and can effectively stabilize the cyclic alkenes in low concentrations.

When a bubbler ampoule is employed as a vaporizer means, a small amount (up to about 10% by weight of the chemical in the ampoule) of accumulated stabilizer is tolerable. This is because bubbler ampoules have a much larger chamber in which chemical is vaporized, and they are designed to be changed out on a fairly regular basis with a fresh bubbler ampoule, though it is advantageous to change them as infrequently as possible.

The compositions and purge methods of the present disclosure exhibit enhanced stability and significantly extend the shelf life of cyclic alkene products, allowing greater flexibility in handling these products in semiconductor manufacturing. The resulting stabilization of cyclic alkenes prevents the possibility of formation of residues (i.e., solidification) of product in the shipping container, in chemical delivery lines, or in valves or a vaporizer means. This lowers equipment maintenance and costs and reduces time the machinery is out of production. In addition, reducing the formation of higher molecular weight compounds allows homogeneous vaporization of the product without concern for the gradual deposition of higher molecular weight compounds in vapor delivery lines, leading to more consistent, higher quality deposited films.

In one embodiment of the present disclosure, the cyclic alkene composition comprises:
a) one or more substituted or unsubstituted cyclic alkenes, and b) an antioxidant compound shown in Formula (I), wherein the antioxidant compound is a phenolic compound and is present in a concentration between 1 ppm and 200 ppm and wherein $R^1$ through $R^5$ can each independently be H, OH, $C_1$-$C_8$ linear, branched, or cyclic alkyl, $C_1$-$C_8$ linear, branched, or cyclic alkoxy or substituted or unsubstituted aryl, wherein said composition is purged with at least one inert gas comprising a gas selected from the group consisting of helium, neon, argon, krypton, xenon, radon, nitrogen, carbon monoxide or carbon dioxide, after said composition is introduced to a container intended for storage or shipping of said composition.

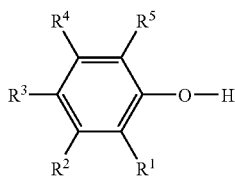

(I)

A cyclic alkene is hereby defined as any carbocyclic compound having a nonaromatic double bond in a nonaromatic ring. Examples of classes of cyclic alkene include, but are not limited to cycloalkenes, cycloalkadienes, cycloalkatrienes, cycloalkatetraenes, aromatic-containing cycloolefins, polycyclic alkenes, polycyclic alkadienes, polycyclic alkatrienes, polycyclic alkatetraenes, and mixtures thereof.

A preferred class of cyclic alkenes are singly or multiply unsaturated cyclic alkenes of the general formula $C_nH_{2n-2x-y}R_y$, where n is the number of carbons in the primary cyclic structure, x is the number of unsaturated sites in the primary cyclic structure, and y is the number of non hydrogen substituents, R, on the primary cyclic structure. In this class of cyclic alkenes, n is an integer from 4 to 18, x is an integer and $1 \leq x \leq n/2$, y is an integer and $0 \leq y \leq 2n-2x$, and each R can independently be $C_1$-$C_{18}$ linear, branched, unsaturated, or cyclic alkyl, $C_1$-$C_{18}$ linear, branched, unsaturated, or cyclic alkoxy, substituted or unsubstituted aryl, or a substituted silicon containing substituent. A more preferred range of values for n is 6 to 14, and a most preferred range is 8 to 12. Examples of this class include, but are not limited to, t-butylcyclohexene, alpha-terpinene, limonene, gamma-terpinene, 1,5-dimethyl-1,5-cyclooctadiene, vinylcyclohexene, cyclobutene, methylcyclobutene, dimethylcyclobutene, trimethylcyclobutene, ethylcyclobutene, diethylcyclobutene, triethylcyclobutene, methoxycyclobutene, methylmethoxycyclobutene, cyclohexylcyclobutene, isopropylcyclobutene, isopropenylcyclobutene, cyclopentene, methylcyclopentene, dimethylcyclopentene, trimethylcyclopentene, methoxycyclopentene, methylmethoxycyclopentene, cyclohexylcyclopentene, isopropylcyclopentene, isopropenylcyclopentene, cyclopentadiene, methylcyclopentadiene, dimethylcyclopentadiene, trimethylcyclopentadiene, methoxycyclopentadiene, methylmethoxycyclopentadiene, cyclohexylcyclopentadiene, isopropylcyclopentadiene, isopropenylcyclopentadiene, cyclohexene, methylcyclohexene, dimethylcyclohexene, trimethylcyclohexene, methoxycyclohexene, methoxymethylcyclohexene, cyclohexylcyclohexene, isopropylcyclohexene, isopropenylcyclohexene, cyclohexadiene, methylcyclohexadiene, dimethylcyclohexadiene, trimethylcyclohexadiene, methoxycyclohexadiene, methoxymethylcyclohexadiene, cyclohexylcyclohexadiene, isopropylcyclohexadiene, isopropenylcyclohexadiene, cycloheptene, methylcycloheptene, dimethylcycloheptene, trimethylcycloheptene, methoxycycloheptene, methoxymethylcycloheptene, cyclohexylcycloheptene, isopropylcycloheptene, isopropenylcycloheptene, cycloheptadiene, methylcycloheptadiene, dimethylcycloheptadiene, trimethylcycloheptadiene, methoxycycloheptadiene, methoxymethylcycloheptadiene, cyclohexylcycloheptadiene, isopropylcycloheptadiene, isopropenylcycloheptadiene, cycloheptatriene, methylcycloheptatriene, dimethylcycloheptatriene, trimethylcycloheptatriene, methoxycycloheptatriene, methoxymethylcycloheptatriene, cyclohexylcycloheptatriene, isopropylcycloheptatriene, isopropenylcycloheptatriene, cyclooctene, methylcyclooctene, dimethylcyclooctene, trimethylcyclooctene, methoxycyclooctene, methoxymethylcyclooctene, cyclohexylcyclooctene, isopropylcyclooctene, isopropenylcyclooctene, cyclooctadiene, methylcyclooctadiene, dimethylcyclooctadiene, trimethylcyclooctadiene, methoxycyclooctadiene, methoxymethylcyclooctadiene, cyclohexylcyclooctadiene, isopropylcyclooctadiene, isopropenylcyclooctadiene, cyclooctatriene, methylcyclooctatriene, dimethylcyclooctatriene, trimethylcyclooctatriene, methoxycyclooctatriene, methoxymethylcyclooctatriene, cyclohexylcyclooctatriene, isopropylcyclooctatriene, isopropenylcyclooctatriene, cyclooctatetraene, methylcyclooctatetraene, dimethylcyclooctatetraene, trimethylcyclooctatetraene, methoxycyclooctatetraene, methoxymethylcyclooctatetraene, cyclohexylcyclooctatetraene, isopropylcyclooctatetraene, isopropenylcyclooctatetraene, 3-phenyl-1-cyclohexene, 3-(2-methoxyphenyl)-1-cyclohexene, 3-cyclohexenyltrimethylsilane, 3-cyclohexenyltrimethoxysilane, [2-(3-cyclohexenyl)ethyl]trimethoxysilane, [2-(3-cyclohexenyl)ethyl]triethoxysilane, tert-butylcyclohexene, p-menth-1-ene, phellandrene, and terpinolene.

Another preferred class of suitable cyclic alkenes is bicyclic alkenes of the general formula $C_nH_{2n-(2x+2)-y}R_y$ where n is the number of carbons in the primary bicyclic structure, x is the number of unsaturated sites in the primary bicyclic structure, and y is the number of non hydrogen substituents, R, on the primary bicyclic structure. In this class of cyclic alkenes, n is an integer from 5 to 18, x is an integer and $x \leq n/2$, y is an integer and $0 \leq y \leq 2n-(2x+2)$, and each R can independently be $C_1$-$C_{18}$ linear, branched, unsaturated or cyclic alkyl, $C_1$-$C_{18}$ linear, branched, unsaturated or cyclic alkoxy, substituted or unsubstituted aryl, or a substituted silicon containing substituent. A more preferred range of values for n is 6 to 14, and a most preferred range is 7 to 12. Examples of this class include, but are not limited to, 3-carene, alpha-pinene, norbornene, norbornadiene, bicyclo[2.2.2]octa-2,5,7-triene, [(bicycloheptenyl)ethyl]trimethoxysilane, hexamethyldewarbenzene, bicyclo[4.3.0]nona-3,7-diene, 1,4,5,8-tetrahydronaphthalene, 2,3-dimethyl-1,4,5,8-tetrahydronaphthalene, bicyclo[4.3.0]nona-3,7-diene, bicyclo[4.1.1]oct-3-ene, bicyclo[4.2.0]oct-3-ene, bicyclo[4.2.0]octa-2,4-diene, 5-(bicyclo[2.2.1]hept-2-enyl)triethoxysilane, bicyclo[4.2.0]octa-2,7-diene, bicyclo[4.3.0]nona-3,6-diene,5-vinyl-2-norbornene and 5-ethylidene-2-norbornene.

Another preferred class of cyclic alkenes is tricyclic alkenes of the general formula $C_nH_{2n-(2x+4)-y}R_y$ where n is the number of carbons in the primary tricyclic structure, x is the number of unsaturated sites in the primary tricyclic structure, and y is the number of non hydrogen substituents, R, on the primary tricyclic structure. In this class, n is an integer from 7 to 18, x is an integer and $x \leq n/2$, y is an integer and $0 \leq y \leq 2n-(2x+4)$, each R can independently be $C_1$-$C_{18}$ linear, branched, unsaturated or cyclic alkyl, $C_1$-$C_{18}$ linear, branched, unsaturated or cyclic alkoxy, substituted or unsubstituted aryl, or a substituted silicon containing substituent. A more preferred range of values for n is 8 to 14, and a most preferred range is 9 to 12. Examples include, but are not limited to, dicyclopentadiene, 1,2,3,4,4A,5,8,8A-octahydro-1,4-methanonaphtalene, octamethyltricyclo[4.2.0.0(2,5)]octa-3,7-diene, 1,4-dihydro-1,4-methanonapthalene and [4.2.2]propella-2,4,7,9-tetraene.

Examples of R in each of the three classes of preferred cyclic alkenes described above include, but are not limited to, methyl, ethyl, propyl, isopropyl, isopropenyl, butyl, phenyl, methylphenyl, trimethylsilyl, cyclohexyl, methoxy, ethoxy, propoxy, isopropoxy, isopropenoxy, butoxy, phenoxy, methylphenoxy, trimethylsiloxy, or cyclohexloxy. Preferred examples of R include methyl, isopropyl, and isopropenyl. Methyl, isopropyl and isopropenyl are most preferred for R for use in semiconductor applications.

Preferred cyclic alkenes include dipentene, phellandrene, dicyclopentadiene, alpha-terpinene, gamma-terpinene, limonene, alpha-pinene, 3-carene, terpinolene, norbornene, norbornadiene, 5-vinyl-2-norbornene, and 5-ethylidene-2-norbornene. The most preferred cyclic alkenes are dicyclopentadiene, alpha-terpinene, norbornene, norbornadiene, 5-vinyl-2-norbornene, and 5-ethylidene-2-norbornene.

Suitable phenolic antioxidants of the disclosure are described by Formula (I) where $R^1$ through $R^5$ can each independently be H, OH, $C_1$-$C_8$ linear, branched, or cyclic alkyl, $C_1$-$C_8$ linear, branched, or cyclic alkoxy or substituted or unsubstituted aryl. Examples of suitable $R^1$ through $R^5$ include, but are not limited to, H, OH, methyl, ethyl, propyl, isopropyl, butyl, isobutyl, tert-butyl, cyclohexyl, methoxy, ethoxy, propoxy, isopropoxy, butoxy, tert-butoxy, cyclohexloxy, phenyl or methylphenyl. Preferred examples of $R^1$ through $R^5$ in Formula (I) include H, OH, methyl, ethyl, methoxy, ethoxy, and tert-butyl. Most preferred examples of $R^1$ through $R^5$ are H and methoxy.

Suitable examples of Formula (I) include, but are not limited to, phenol, 4-methylphenol, 3-methylphenol, 2-methylphenol, 4-ethylphenol, 4-propylphenol, 4-iso-propylphenol, 4-butylphenol, 4-sec-butylphenol, 4-iso-butylphenol, 4-tert-butylphenol, 4-methoxyphenol, 3-methoxyphenol, 2-methoxyphenol, 4-ethoxyphenol, 2-(1-methylbutyl)phenol, 2-tert-butyl-6-methylphenol, and 1,2-dihydroxybenzene. Preferred antioxidants of Formula (I) include phenol, 4-methylphenol, 3-methylphenol, 2-methylphenol, 4-methoxyphenol, 3-methoxyphenol, 2-methoxyphenol, 2,4-di-tert-butylphenol, 2,6-di-tert-butyl-4-methylphenol (BHT), 1,3-dihydroxybenzene, hydroquinone, 2-(benzyloxy)phenol, 3,4,5-trimethoxyphenol, 3-ethoxy-4-methylphenol, 4-benzyloxyphenol, 4-benzyl-2,6-di-tert-butylphenol, 2-(2-butenyl)phenol, 4-propoxyphenol, 4-butoxyphenol, 2-(4-methylbenzyl)phenol, 2,4,6-tris-benzyloxyphenol, 2,4-dicyclohexyl-5-methylphenol, and 6-tert-butyl-1,2-dihydroxybenzene. The most preferred antioxidants of Formula (I) are 4-methoxyphenol (MHQ) and 2,6-di-tert-butyl-4-methylphenol (BHT).

A suitable concentration of phenolic additive may be obtained from a range of concentrations, such as from about 1 ppm to about 200 ppm. Suitable concentration ranges can be defined by defining a low end of suitable concentrations and a high end of suitable concentrations.

The low end of the suitable concentration range for the phenolic additive may be from about 1 ppm to about 50 ppm. Suitable concentrations for the low end concentration range include, but are not limited, to about 1 ppm, about 5 ppm, about 10 ppm, about 25 ppm and about 50 ppm.

The high end of the suitable concentration range is not critical for stabilization of the compositions, but may be limited by some considerations of the deposited film purity and solubility of the phenolic additive in the cyclic alkene composition. A suitable concentration range for the high end phenolic additive concentration may be from about 100 ppm to about 200 ppm. Examples of suitable concentrations for the high end include but are not limited to about 100 ppm, about 125 ppm, about 150 ppm, about 175 ppm and about 200 ppm.

Suitable concentration ranges may vary depending on the specific antioxidant employed and the specific process used. Examples of suitable concentration ranges include from about 1 ppm to about 200 ppm, from about 1 ppm to about 150 ppm, from about 1 ppm to about 100 ppm. Other suitable concentration ranges would include from about 10 ppm to about 200 ppm, from about 10 ppm to about 175 ppm, from about 10 ppm to about 125 ppm, and from about 10 ppm to about 100 ppm. Other suitable concentration ranges would include from about 25 ppm to about 200 ppm, from about 25 ppm to about 175 ppm, from about 25 ppm to about 125 ppm, and from about 25 ppm to about 100 ppm. Other suitable concentration ranges would include from about 50 ppm to about 200 ppm, from about 50 ppm to about 175 ppm, about 50 ppm to about 150 ppm, from about 50 ppm to about 125 ppm, and from about 50 ppm to about 100 ppm.

The stabilized cyclic alkene composition may include a single phenolic additive or a mixture of two or more phenolic additives having Formula (I). The mixture of two or more phenolic additives may be present in any relative proportion to each other.

The cyclic alkenes can be obtained commercially or by synthetic techniques known to those in the art. In commercial materials chemical manufacturers who make cyclic alkenes, will often stabilize their products with relatively high concentrations of BHT. Since most manufacturers are not accustomed to making high purity products, their product handling techniques can be relatively poor, and air, moisture and other contaminants can possibly enter the container before, during or after filling. These contaminants, once closed off into the container, can cause considerable degradation to the product if it is stored for any length of time. For semiconductor purposes, the commercial materials must be purified to remove all byproducts, and additives, usually by distillation or sublimation.

However, to maintain purity and stabilization during purification, storage, and shipping, the cyclic alkene and compositions of the disclosure must be handled under strictly controlled conditions. These may include: addition of stabilizer to the product receiver prior to distillation so that product is immediately stabilized once it enters the product receiver, performing distillations and handling purified products under dry, inert atmospheres using common inert gases such as nitrogen or argon (but not uncommon inert gases such as carbon dioxide or carbon monoxide), rigorously cleaning and drying containers before use, purging containers with inert atmosphere of the common inert gases prior to and after filling, using closed-filling techniques that prevent the product from being exposed to air, filling in a cleanroom to avoid dust and trace metal contamination that could act as polymerization catalysts, and judicious choice of containers to prevent exposure to air or other incompatible materials.

Many chemical precursors and precursor compositions for the semiconductor industry are typically packaged, shipped and stored in stainless steel containers to retain product quality for the maximum amount of time. It is advantageous to purge containers of air using inert gases prior to filling. However, despite rigorous efforts to exclude air during the purge process prior to filling and during the fill process, adventitious air and other reactive gases inevitably make their way in to a container. Thus, after the container is filled and just prior to sealing the container, a post-fill purge cycle is necessary for sensitive chemicals, such as cyclic alkenes. An effective purge cycle is designed to displace the majority of adventitious air and other reactive gases from the container, leaving the stabilized cyclic alkene composition primarily with inert gas in the headspace of the container and dissolved in the composition.

It is advantageous to purge the container with an inert gas prior to sealing the container for storage or shipment. The inert gases that can be used include, but are not limited to, helium, neon, argon, krypton, xenon, radon, nitrogen, carbon monoxide or carbon dioxide and mixtures thereof. The preferred inert gases for purging containers are helium, argon, nitrogen, carbon monoxide and carbon dioxide. The more preferred inert gases for purging containers are helium, nitrogen, carbon monoxide and carbon dioxide. The most preferred inert gas for purging containers is carbon dioxide.

It is preferable to purge the stabilized cyclic alkene composition immediately after it is packaged to prevent decomposition due to dissolved gases or adventitious air. The composition may be purged, however, at any time after the container is filled and before it is sealed prior to storage or shipment. The composition may be purged by a number of different techniques including, but not limited to, purging gas through the composition using a tube submerged in the composition, purging the headspace of the container, evacuating the headspace of the container using vacuum and refilling the headspace with the purge gas, pressurizing the headspace of the container with pressurized purge gas and releasing the pressure, repetitions of such processes, and combinations of such processes. The most preferred method to purge the composition is to purge gas through the composition using a tube submerged in the composition. Purge techniques can optionally result in the intentional pressurization of the sealed container following a purge cycle to further prevent the permeation of adventitious air into the container. It is preferable, but not necessary, to seal a container under pressure after it is purged.

Purge times for each process can vary based on the desired effect, where longer purge times are recommended to remove more adventitious gases. Purge times can range on the order of seconds to hours depending on the flow rates used. For example, the purge time can range from 10 seconds to 5 minutes.

Techniques to purge gas through the composition using a tube submerged in the composition can additionally include the use of a diffusive device to aid in diffusing the purge gas into the liquid. Diffusive devices are constructs that have more than one outlet for gas to escape from, most preferably a large multitude of outlets as found in porous diffusion stones. Diffusive devices can include tubes having a plurality of holes or porous diffusion stones fabricated from glass, metal or plastic.

Those skilled in the art generally associate the term "inert gas" with helium, neon, argon, krypton, xenon, radon and nitrogen while carbon monoxide or carbon dioxide are not. Indeed, under certain conditions, carbon monoxide and carbon dioxide may be defined as reactive or oxidizing. However, their behavior as such is primarily dependent on the conditions under which they are used. At room temperature with no other energy source present, they can be considered as being inert when used as a packaging gas.

The compositions of the disclosure may be used in any suitable chemical vapor deposition process which requires a cyclic alkene. Preferred processes are those chemical vapor deposition processes employing a silicon containing compound to deposit a low dielectric constant film. Examples of suitable processes include, but are not limited to those described in U.S. Pat. Nos. 6,815,373, 6,596,627, 6,756,323, 6,541,398, 6,479,110, 6,846,515, and 6,583,048, herein incorporated by reference.

The present disclosure is also directed to a process of using a cyclic alkene composition for forming a layer of carbon-doped silicon oxide on a wafer. The process comprises the steps of:

a) providing a cyclic alkene composition in a container, a silicon containing compound in a container, a film deposition tool, a film deposition chamber within said film deposition tool, a means for connecting the containers to the film deposition chamber within said film deposition tool, a stream of carrier gas to sweep the cyclic alkene composition and the silicon containing compound through the connecting means into the film deposition chamber, and a substrate within the film deposition chamber of the film deposition tool;

b) introducing the vapors of the cyclic alkene composition and the silicon containing compound into the carrier gas stream;

c) transporting the vapor of the cyclic alkene composition and silicon containing compound into the film deposition chamber; and d) using one or more energy means, to form a carbon doped silicon oxide film on the substrate, wherein said cyclic alkene composition comprises:

1) one or more substituted or unsubstituted cyclic alkenes, and 2) an antioxidant composition comprising at least one compound of Formula (I), wherein the antioxidant composition is present in a concentration between 1 ppm and 200 ppm, and wherein $R^1$ through $R^5$ can each independently be H, OH, $C_1$-$C_8$ linear, branched, or cyclic alkyl, $C_1$-$C_8$ linear, branched, or cyclic alkoxy or substituted or unsubstituted aryl, wherein said composition is purged with at least one inert gas comprising a gas selected from the group consisting of helium, neon, argon, krypton, xenon, radon, nitrogen, carbon monoxide or carbon dioxide, after said composition is introduced to a container intended for storage or shipping of said composition.

The cyclic alkenes suitable for this disclosure are the same as described previously (vide supra).

Silicon containing compounds suitable for this disclosure include any class of silicon containing molecule such as silanes, alkylsilanes, alkoxysilanes, alkylalkoxysilanes, carboxysilanes, alkylcarboxysilanes, alkoxycarboxysilanes, alkylalkoxycarboxysilanes, linear siloxanes, cyclic siloxanes, fluorinated silanes, fluorinated alkylsilanes, fluorinated alkoxysilanes, fluorinated alkylalkoxysilanes, fluorinated carboxysilanes, fluorinated alkylcarboxysilanes, fluorinated alkoxycarboxysilanes, fluorinated alkylalkoxycarboxysilanes, fluorinated linear siloxanes, fluorinated cyclic siloxanes, and mixtures thereof. Examples of each class described above include, but are not limited to, those shown in Scheme 1.

Scheme 1

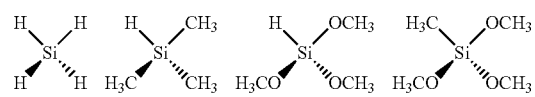

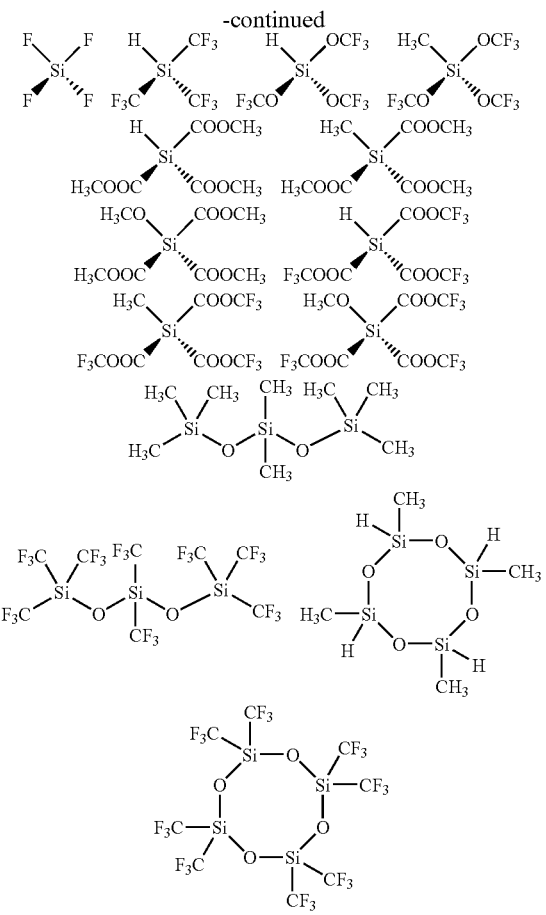

Suitable examples of silicon containing compounds of the disclosure are those described by Formula (II). In Formula (II), $R^6$ through $R^9$ can each independently be H,

F, OH, $C_1$-$C_8$ linear, branched or unsaturated alkyl, $C_1$-$C_8$ linear, branched or unsaturated, alkoxy, substituted or unsubstituted cyclic or cyclic alkoxy, substituted or unsubstituted aryl or aryl alkoxy, substituted silicon containing substituent, partially or fully fluorinated $C_1$-$C_8$ linear, branched or unsaturated alkyl, partially or fully fluorinated $C_1$-$C_8$ linear, branched, unsaturated alkoxy, partially or fully fluorinated substituted or unsubstituted cyclic or cyclic alkoxy, partially or fully fluorinated substituted or unsubstituted aryl or aryl alkoxy, partially or fully fluorinated substituted silicon containing substituent, non-, partially or fully fluorinated carboxylate ligands, or mixtures thereof. Examples of $R^6$ through $R^9$ in Formula (II) include, but are not limited to, H, F, OH, methyl, ethyl, propyl, isopropyl, isopropenyl, butyl, phenyl, methylphenyl, cyclohexyl, methylcyclohexyl, methoxy, ethoxy, propoxy, isopropoxy, butoxy, phenoxy, methylphenoxy, cyclohexyloxy, methylcyclohexyloxy, trifluoromethyl, trifluoroethyl, penatafluoroethyl, trifluoropropyl, pentafluoropropyl, heptafluoropropyl, isopropyl, hexafluoroisopropyl, trifluoroisopropenyl, trifluorobutyl, pentafluorobutyl, nonafluorobutyl, trifluorophenyl, (trifluoromethyl)tetrafluorophenyl, undecafluorocyclohexyl, (trifluoromethyl)decafluorocyclohexyl, trifluoromethoxy, trifluoroethoxy, pentafluoroethoxy, trifluoropropoxy, pentafluoropropoxy, heptafluoropropoxy, hexafluoroisopropoxy, heptafluoroisopropoxy, trifluorobutoxy, pentafluorobutoxy, nonafluorobutoxy, pentafluorophenoxy, (trifluoromethyl)tetrafluorophenoxy, undecafluorocyclohexyloxy, (trifluoromethyl)decafluorocyclohexyloxy, dimethylsiloxy (in the case of linear siloxanes), trimethylsiloxy, trimethyldisiloxy, pentamethyldisiloxy, diethylsiloxy, triethylsiloxy, triethyldisiloxy, pentaethyldisiloxy, dimethoxysiloxy, trimethoxysiloxy, trimethoxydisiloxy, pentamethoxydisiloxy, diethoxysiloxy, triethoxysiloxy, triethoxydisiloxy, pentaethoxydisiloxy, $\eta^2$-trimethyltrisiloxy (in the case of cyclic siloxanes, such as tetramethylcyclotetrasiloxane) and $\eta^2$-hexamethyltrisiloxy (in the case of cyclic siloxanes, such as octamethylcyclotetrasiloxane). Preferred examples of $R^6$ through $R^9$ include H, F, methyl, methoxy, ethyl, ethoxy and siloxy. For Formula (II), H, methyl, ethoxy and substituted siloxy are most preferred for $R^6$ through $R^9$ for use in semiconductor applications.

Examples of silicon containing compounds suitable for this disclosure include, but are not limited to, silane, methylsilane, dimethylsilane, trimethylsilane, tetramethylsilane, ethylsilane, diethylsilane, triethylsilane, tetraethylsilane, propylsilane, dipropylsilane, tripropylsilane, tetrapropylsilane, isopropylsilane, diisopropylsilane, triisopropylsilane, tetraisopropylsilane, butylsilane, dibutylsilane, tributylsilane, tetrabutylsilane, methyltrimethoxysilane, dimethyldimethoxysilane, trimethylmethoxysilane, trimethoxysilane, tetramethoxysilane, methylmethoxysilane, methyidimethoxysilane, methyltriethoxysilane, dimethyldiethoxysilane, trimethylmethoxysilane, tetraethoxysilane, methylethoxysilane, methyldiethoxysilane, methylpropoxysilane, dimethyldipropoxysilane, trimethylpropoxysilane, tetrapropoxysilane, methyltriisopropoxysilane, dimethyldiisopropoxysilane, trimethylisopropoxysilane, tetraisopropoxysilane, methyldiisopropoxysilane, methylphenylsilane, methyldiphenylsilane, methyltriphenylsilane, dimethyldiphenylsilane, trimethylphenylsilane, methyl (methylphenyl)silane, methyidi(methylphenyl)silane, methyltri(methylphenyl)silane, methylphenoxysilane, methyldiphenoxysilane, dimethyldiphenoxysilane, methyl(methylphenoxy)silane, methyidi(methylphenoxy)silane, dimethyldi(methylphenoxy)silane, methyl(cyclohexyl)silane, methyldi(cyclohexyl)silane, methyltri(cyclohexyl)silane, dimethyldi(cyclohexyl)silane, trimethyl(cyclohexyl)silane, methyl(methylcyclohexyl)silane, methyldi(methylcyclohexyl)silane, methyltri(methylcyclohexyl)silane, dimethyldi(methylcyclohexyl)silane, trimethyl(methylcyclohexyl)silane, methyl(cyclohexyloxy)silane, methyidi(cyclohexyloxy)silane, methyl(tricyclohexyloxy)silane, dimethyidi(cyclohexyloxy)silane, methyl(methylcyclohexyloxy)silane, methyidi(methylcyclohexyloxy)silane, methyltri(methylcyclohexyloxy)silane, dimethyldi(methylcyclohexyloxy)silane, silicon tetrafluoride, fluorotrimethylsilane, methyltris(trifluoromethoxy)silane, trifluoromethyltris(trifluoromethoxy)silane, fluorotriethoxysilane, triacetoxysilane, methoxytriacetoxysilane, vinyltriacetoxysilane, vinylmethyldiacetoxysilane, trimethylsilyl(trimethylsilyl)propynoate, trimethylsilyl(trimethylsiloxy)acetate, trimethylsilyltrifluoroacetate, tris(trifluoromethylsilyl)trifluoroacetate, triethylacetoxysilane, tri(trifluoroacetoxy)silane, methyltri(trifluoroacetoxy)silane, methoxytri(trifluoroacetoxy)silane, tetra(trifluoroacetoxy)silane, tetraacetoxysilane, phenyltriacetoxysilane, phenyldimethylacetoxysilane, phenyldimethoxyacetoxysilane, phenylacetoxytrimethylsilane, 1,1,1,3,3-pentamethyl-3-acetoxydisiloxane, methyltriacetoxysilaneethyltriacetoxysilane, methyltriacetoxysilane, methacryloxytrimethylsilane, ethyltriacetoxysilane, dimethyidiacetoxysilane, di-t-butoxydiacetoxysilane, dibenzyloxydiacetoxysilane, bis(trimethylsilyl)malonate, bis(trimethylsilyl)acetylenedicarboxylate, acryloxytrimethylsilane, acetoxytrimethylsilane, acetoxymethyidimethylacetoxysilane, triethyl(trifluoroacetoxy)silane, phenyltri(trifluoroacetoxy)silane, phenyldi(trifluoromethyl)acetoxysilane, (pentafluorophenyl)dimethylacetoxysilane, phenyldimethyl(trifluoroacetoxy)silane, phenyl(trifluoroacetoxy)trimethylsilane, (trifluorophenyl)acetoxytrimethylsilane, phenylacetoxytri(trifluoromethyl)silane 1,1,1,3,3-penta(trifluoromethyl)-3-acetoxydisiloxane, (trifluoromethyl)triacetoxysilaneethyltriacetoxysilane, (trifluoromethyl)triacetoxysilane, (trifluoromethyl)(trifluoromethoxy)diacetoxysilane, methacryloxytri(trifluoromethyl)silane, (trifluoroethyl)triacetoxysilane, di(trifluoromethyl)diacetoxysilane, di-(nonafluoro-t-butoxy)diacetoxysilane, dibenzyloxydi(trifluoroacetoxy)silane, acryloxytri(trifluoromethyl)silane, acetoxytri(trifluoromethyl)silane, acetoxy(trifluoromethyl)dimethylacetoxysilane, (trifluoromethyl)silane, di(trifluoromethyl)silane, tri(trifluoromethyl)silane, tetra(trifluoromethyl)silane, (trifluoroethyl)silane, di(trifluoroethyl)silane, tri(trifluoroethyl)silane, tetra(trifluoroethyl)silane, (trifluoropropyl)silane, di(trifluoropropyl)silane, tri(trifluoropropyl)silane, tetra(trifluoropropyl)silane, (hexafluoroisopropyl)silane, di(hexafluoroisopropyl)silane, tri(hexafluoroisopropyl)silane, tetra(hexafluoroisopropyl)silane, (trifluorobutyl)silane, di(trifluorobutyl)silane, tri(trifluorobutyl)silane, tetra(trifluorobutyl)silane, (trifluoromethyl)trimethoxysilane, di(trifluoromethyl)dimethoxysilane, tri(trifluoromethyl)methoxysilane, tetra(trifluoromethoxy)silane, (trifluoromethyl)methoxysilane, (trifluoromethyl)dimethoxysilane, (trifluoromethyl)triethoxysilane, di(trifluoromethyl)diethoxysilane, tri(trifluoromethyl)methoxysilane, tetra(trifluoroethoxy)silane, (trifluoromethyl)ethoxysilane, (trifluromethyl)diethoxysilane, (trifluoromethyl)propoxysilane, di(trifluoromethyl)dipropoxysilane, tri(trifluoromethyl)propoxysilane, tetra(trifluropropoxy)silane, (trifluoromethyl)triisopropoxysilane, di(trifluoromethyl)diisopropoxysilane, tri(trifluoromethyl)isopropoxysilane, tetra(trifluoroisopropoxy)silane, (trifluoromethyl)diisopropoxysilane, (trifluoromethyl)phenylsilane, (trifluoromethyl)diphenylsilane, (trifluoromethyl)triphenylsilane, di(trifluoromethyl)diphenylsilane, tri(trifluoromethyl)phenylsilane, (trifluoromethyl)(methylphenyl)silane, (trifluoromethyl)di(methylphenyl)silane, (trifluoromethyl)tri(methylphenyl)silane, (trifluoromethyl)phenoxysilane, (trifluoromethyl)diphenoxysilane, di(trifluoromethyl)diphenoxysilane, (trifluoromethyl)(methylphenoxy)silane, (trifluoromethyl)di(methylphenoxy)silane, di(trifluoromethyl)di(methylphenoxy)silane, (trifluoromethyl)(cyclohexyl)silane, (trifluoromethyl)di(cyclohexyl)silane, (trifluoromethyl)tri(cyclohexyl)silane, di(trifluoromethyl)di(cyclohexyl)silane, tri(trifluoromethyl)(cyclohexyl)silane, (trifluoromethyl)(methylcyclohexyl)silane, (trifluoromethyl)di(methylcyclohexyl)silane, (trifluoromethyl)tri(methylcyclohexyl)silane, di(trifluoromethyl)di(methylcyclohexyl)silane, tri(trifluoromethyl)(methylcyclohexyl)silane, (trifluoromethyl)(cyclohexyloxy)silane, (trifluoromethyl)di(cyclohexyloxy)silane, (trifluoromethyl)tri(cyclohexyloxy)silane, di(trifluoromethyl)di(cyclohexyloxy)silane, (trifluoromethyl)(methylcyclohexyloxy)silane, (trifluoromethyl)di(methylcyclohexyloxy)silane, (trifluoromethyl)tri(methylcyclohexyloxy)silane, di(trifluoromethyl)di(methylcyclohexyloxy)silane, tri(trifluoromethoxy)silane, methyltri(trifluoromethoxy)silane, dimethyidi(trifluoromethoxy)silane, trimethyl(trifluoromethoxy)silane, methyl(trifluormethoxy)silane, methyldi(trifluoromethoxy)silane, methyltri(trifluoroethoxy)silane, dimethyidi(trifluoroethoxy)silane, trimethyl(trifluoromethoxy)silane, methyl(trifluoroethoxy)silane, methyldi(trifluoroethoxy)silane, methyl(trifluoropropoxy)silane, dimethyldi(trifluoropropoxy)silane, trimethyl(trifluoropropoxy)silane, methyltri(hexafluoroisopropoxy)silane, dimethyldi(hexafluoroisopropoxy)silane, trimethyl(hexafluoroisopropoxy)silane, methyldi(hexafluoroisopropoxy)silane, methyl(pentafluorophenyl)silane, methyidi(pentaphenyl)silane, methyltri(pentaphenyl)silane, dimethyl(pentafluorophenyl)silane, trimethyl(pentafluorophenyl)silane, methyl[(trifluoromethyl)phenyl]silane, methyldi[(trifluoromethyl)phenyl]silane, methyltri[(trifluoromethyl)phenyl]silane, methyl(pentafluorophenoxy)silane, methyidi(pentafluorophenoxy)silane, dimethyldi(pentafluorophenoxy)silane, methyl[(trifluoromethyl)phenoxy]silane, methyldi[(trifluoromethyl)phenoxy]silane, dimethyldi[(trifluoromethyl)phenoxy]silane, methyl(undecafluorocyclohexyl)silane, methyldi(undecafluorocyclohexyl)silane, methyltri(undecafluorocyclohexyl)silane, dimethyldi(undecafluorocyclohexyl)silane, trimethyl(undecacyclohexyl)silane, methyl[(trifluoromethyl)cyclohexyl]silane, methyldi[(trifluoromethyl)cyclohexyl]silane, methyltri[(trifluoromethyl)cyclohexyl]silane, dimethyldi[(trifluoromethyl)cyclohexyl]silane, trimethyl[(trifluoromethyl)cyclohexyl]silane, methyl(undecafluorocyclohexyloxy)silane, methyldi(undecafluorocyclohexyloxy)silane, methyltri(undecafluorocyclohexyloxy)silane, dimethyidi(undecafluorocyclohexyloxy)silane, methyl[(trifluoromethyl)cyclohexyloxy]silane, methyidi[(trifluoromethyl)cyclohexyloxy]silane, methyltri[(trifluoromethyl)cyclohexyloxy]silane, dimethyldi[(trifluoromethyl)cyclohexyloxy]silane, hexamethyldisiloxane, octamethyltrisiloxane, octa(trifluoromethyl)trisiloxane, trimethyltrisiloxane, diethyltrimethyltrisiloxane, trimethylcyclotrisiloxane, tetramethylcyclotetrasiloxane, pentamethylcyclopentasiloxane, tetraethylcyclotetrasiloxane, pentaethylcyclopentasiloxane, hexamethylcyclotrisiloxane, octamethylcyclotetrasiloxane, decamethylcyclopentasiloxane, vinylmethyidiethoxysilane vinylmethyidimethoxysilane, trimethylsilylacetylene, di(trimethylsilyl)acetylene, hexa(trifluoromethyl)disiloxane, octa(trifluoromethyl)trisiloxane, tris(trifluoromethyl)trisiloxane, tris(trifluoromethyl)cyclotrisiloxane, tetra(trifluoromethyl)cyclotetrasiloxane, octa(trifluoromethyl)cyclotetrasiloxane and mixtures thereof.

Preferred examples of silicon containing compounds in Formula (II) include trimethylcyclotrisiloxane, triethylcyclotrisiloxane, tetramethylcyclotetrasiloxane, tetraethylcyclotetrasiloxane, pentamethylcyclopentasiloxane, pentaethylcyclopentasiloxane, octamethylcyclotetrasiloxane, methyltriethoxysilane, vinylmethyidimethoxysilane, vinylmethyidiethoxysilane, trimethylsilylacetylene, bis(trimethylsilyl)acetylene, methyldimethoxysilane and methyidiethoxsilane. Tetramethylcyclotetrasiloxane, methyldiethoxysilane, dimethyldimethoxysilane and trimethylsilylacetylene are most preferred for use in the semiconductor industry.

Figure 2:
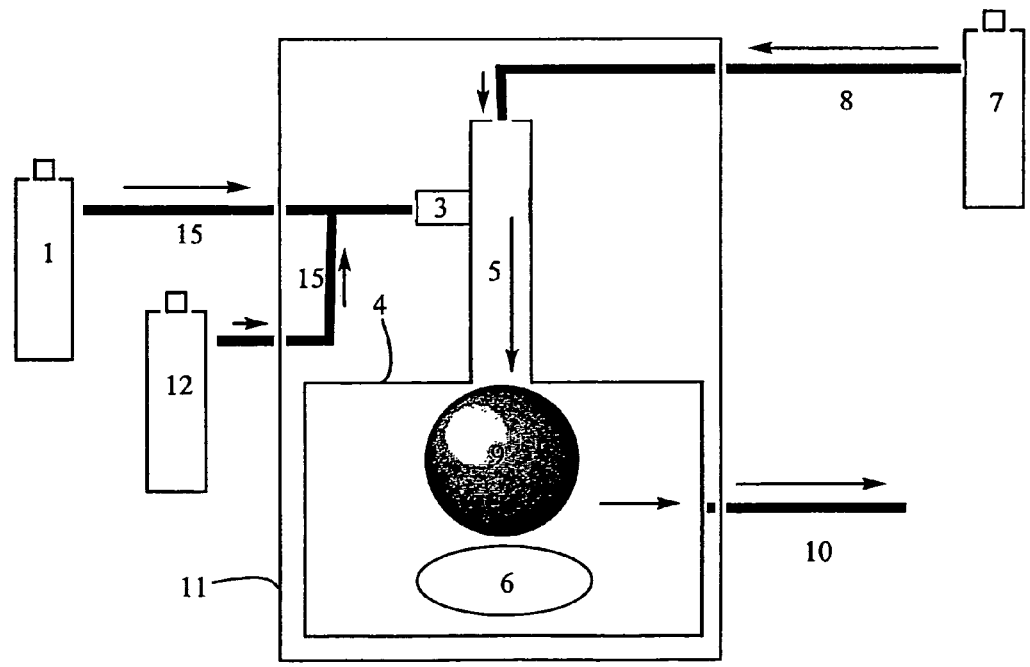
FIG. 2 is a representation of a film deposition tool used in the semiconductor industry for use with the compositions according to the present disclosure, where a single vaporizer means is used with two separate precursors.

In a typical chemical vapor deposition process requiring at least two precursors, there are several methods by which the components can be combined. Referring to FIGS. 1 and 2, such a process is shown. One precursor (e.g., a cyclic alkene) is transported from a container (1), through chemical delivery lines (2), to a vaporizer means (3) housed in the film deposition tool (11). The precursor can be transported from the container (1) through the delivery line (2) to the vaporizer means (3) by a variety of techniques, including, but not limited to, pressurization of the container with an inert gas, use of a mechanical pumping mechanism, gravity feed, or combinations thereof. The second precursor (e.g., a silicon containing compound) is transported from a separate container (12), through chemical delivery lines (13), to a vaporizer means (14) housed in the film deposition tool (11). The second precursor can be transported from the container (12) through the delivery line (13) to the vaporizer means (14) by a variety of techniques, including, but not limited to, pressurization of the container with an inert gas, use of a mechanical pumping mechanism, gravity feed, or combinations thereof.

In the event that the second precursor (e.g., a silicon containing compound) is a gas at room temperature, or it requires substantially little or no energy to be vaporized as it is introduced into the chemical vapor process line (5), a second vaporizer means (14) may instead have the form of a valve, check valve, baffle, diffusing apparatus or similar device meant to infuse gas into a tube or chamber without a means to enable vaporization.

It is important to note that, while it is desirable to have at least one vaporizer means (3) attached to a chemical vapor process line (5), it is also possible to connect at least one vaporizer means (3) directly to the deposition chamber (4), optionally connecting one or more additional vaporizer means (14) to a chemical vapor process line (5) or directly to the deposition chamber (4). Additionally, a gas delivery line (8) may optionally be connected directly to the deposition chamber (4). In the event that no vaporizer means (3, 14) or gas delivery lines (8) are connected to a chemical vapor process line (5), the chemical vapor process line becomes a feature that is optionally attached to the deposition chamber (4).

Ideally, separate chemical delivery lines and vaporizer means are used for each precursor, however it is possible for two precursors to be vaporized using a single vaporizer means when the two precursors are chemically compatible. When using a single vaporizer means (3) both precursors are combined or separately dispensed through a portion of the chemical delivery line (15) to the vaporizer means (3). When the two precursors are combined prior to vaporization, as shown in FIG. 2, the process simply involves their combination in the chemical delivery line (15), followed by vaporization of the two precursors in the vaporizer means (3). When the two precursors are separately dispensed through a single vaporizer means (3), the sequence to dispense each precursor could simply involve flow of one precursor through the chemical delivery line (15) to the vaporizer means (3) followed by flow of a second precursor through the chemical delivery line (15) to the vaporizer means (3) without repetition. Alternatively, there may be a need to flow one precursor, flow the second precursor, and repeat these steps until the desired layer is formed. The process used is wholly dependent on the film properties desired. In the event that only one vaporizer means (3) is used, the second vaporizer means (14) is not needed.

In a process of flowing two different precursors through separate chemical lines and vaporizer means, a suitable precursor flow rate for each precursor can range from about 0.01 to about 10 mL/minute. The vaporizer means (3, 14) serves as a means to convert liquid precursor to a vapor or mist, and it can use various techniques, such as heat, high pressure gas, or other means to accomplish this task. Alternatively, the vaporizer means (3, 14) may consist of a container that holds a volume of liquid, through which an inert gas is flowed as a means to (a) convert the precursor from a liquid to a vapor, and (b) transport the precursor vapor into the chemical vapor process line (5). Regardless of the vaporizer means (3, 14) design, the conversion of the precursor from liquid to gaseous state may take place either in the vaporizer means (3, 14) or in the chemical vapor process line (5) The precursor is injected in the form of a vapor or mist into the chemical vapor process line (5) that is commonly heated between about 30° C. and about 120° C. to prevent the precursor vapor from condensing inside the line (5). Mixing of the precursor components can take place in the chemical vapor process line (5), or in different locations within the deposition chamber (4), depending on where the vaporizer means (3, 14) are located with respect to one another. The chemical vapor process line (5) is connected to the deposition chamber (4) inside the film deposition tool (11), and substrate (6) is housed within the deposition chamber (4). The deposition chamber (4) and chemical vapor process line (5) may be operated at ambient pressure (i.e., 760 torr), but it is also common to operate below atmospheric pressure, from about 0.01 torr to about 700 torr, to enhance vaporization of the precursors and to help keep the precursors in the vapor phase.

It should be understood by those skilled in the art that the connection between the chemical vapor process line (5) and the deposition process chamber (4) can vary from deposition tool to deposition tool, depending on the requirements for the process. For example, designs may include various apparatuses that affect the mixing, heating, cooling, or distribution of gases within the system. These may include an apparatus having baffles to mix the gases, a heated zone to heat gases, a cooling zone to cool gases, a chamber to allow pressure equilibration, or a showerhead to distribute gases over the surface of a wafer. Designs may, for example, route chemical vapors from the chemical vapor process line (5) through a baffled mixing apparatus, through a heated zone and through a showerhead before the gases are passed to the substrate (6) in the deposition chamber (4). Due to the complexity of designs that are available in the market and their variability based on need driven by the process, the options are described only in general terms here.

In our general example, the precursor vapors are transported through the chemical vapor process line (5) to the substrate (6) in the deposition chamber (4) by a stream of gas flowing past the vaporizer means (3, 14). The stream of gas is supplied from a source tank (7) and flows through a gas delivery line (8) to the chemical vapor process line (5). The stream of gas, having a flow rate of about 5 sccm to about 10,000 sccm, is often heated to enhance vaporization of the precursors to help keep the precursors in the vapor phase. The gas used may be inert, such as nitrogen, helium or argon, chosen simply to act as a means to transport the precursor vapor to the substrate, or it may be a reactive gas, such as oxygen, ozone, ammonia, nitrous oxide, carbon dioxide, carbon monoxide, $SiH_4$, silanes, silicon tetrafluoride, hydrazine and the like to enhance the deposition process.

As the precursor vapors are transported to the substrate (6), they may be mixed with one or more reactants, in addition to the transport gas, to enhance its deposition onto the substrate. The reactants may be reactive gases as mentioned above, or they may be other chemical precursors such as amines, aminoalcohols, alkanes, alkenes, alkynes, alcohols, esters, ketones, aldehydes, carboxylic acids and the like. The reactants are carefully selected to enhance the deposition of precursor on the substrate, and to modify the chemical identity and properties of the layer deposited onto the substrate. These reactants can be introduced into the film deposition tool (11) by various means and at various locations in the process, depending on the desired effect. It is most convenient to introduce a reactant into the film deposition tool (11) in gaseous form, so it would be necessary to have an additional vaporizer means in the case where liquid reactants are used. An additional vaporizer means, or gas delivery line used to introduce a reactant can be placed near the point where the gas delivery line (8) meets the chemical vapor process line (5), upstream or downstream of the vaporizer means, directly into or near the plasma (9), and/or somewhere on the sides, top, or bottom of the film deposition chamber (4) of the film deposition tool (11).

The precursor vapors, potential reactants, and inert or reactive gases may also experience other conditions used to enhance deposition, such as heat or plasma (9). The precursor vapor may be preheated to between about 50° C. and about 800° C. before contact with the substrate to enhance the deposition of the precursors on the substrate. A plasma may also be used to add energy to the precursor vapors and enhance the deposition. Additionally, the plasma may be pulsed on and off to change the properties of the deposited film. The plasma power and pulse duration are carefully selected to enhance the deposition of the precursors on the substrate, and to modify the chemical identity and properties of the layer deposited onto the substrate. The plasma may also be applied over a range of frequencies, where the high and low frequency plasma power may range from about 0 to several kilowatts. The substrate may also have a bias of between about 0 and about −400 VDC to enhance material transport to the substrate. The substrate may be heated from about 25° C. to about 500° C. to either cause thermal breakdown of the precursor on the substrate, or may be used to enhance the deposition of precursor on the substrate. Unreacted materials are exhausted through an exhaust line (10).

The elemental composition of the film, and thus the film properties, can be adjusted by the choice of starting silicon containing compound, the cyclic alkene employed, and the use or lack of use of various reactive gases in the process.

Subsequent to the film deposition, the initial film may be subjected to a curing step. The curing steps may also be employed to modify e.g. the density or elemental compositions of the films to change film properties such as film strength, dielectric constant and various other properties of the film. These curing steps may comprise a thermal treatment by the application of heat through one of various heating means such as hot plates, ovens, infrared lamps, or microwaves. Alternatively, the curing may comprise a plasma treatment, or a chemical treatment of the film. These curing steps may take place in an inert atmosphere (e.g. noble gases), a reducing atmosphere (e.g. hydrogen, or hydrocarbon), or an oxidizing atmosphere (e.g. oxygen, air, ozone, nitrous oxide, carbon dioxide) depending on the desired chemical change in the initial film. Such processes are described in the art and known to those skilled in the art.

EXAMPLES

Comparative Examples 1-7

A series of tests were devised to compare the decomposition of pure NBDE under various conditions against NBDE which has been stabilized with an additive. In these tests, glass ampoules were filled with approximately 50 mL of stabilized or unstabilized NBDE, leaving approximately 15 mL of headspace. The samples were prepared in a nitrogen-purged glovebox to prevent exposure to adventitious gases before the experiment. The headspace of each container was then purged three times with room air over the course of 5 seconds prior to the container being sealed at ambient pressure.

Samples were then exposed to temperatures of 60 or 80° C. for a period of 24 hours to simulate accelerated decomposition conditions. After the experiment was complete, the volatiles in each ampoule were removed in vacuo at room temperature, and the non-volatile decomposition products remained behind. The extent of decomposition, or residue formation, was determined by comparing the mass of the container after the experiment to the mass of the container before the experiment. The difference between the two masses is the amount of decomposition that resulted in the sample under those conditions. The mass of the additive was subtracted out to give a result that only represents the decomposition that occurred, and the final mass was multiplied by 20 to give the amount of solid that would be found in 1 L of sample.

Results outlined in Table 1 show that for pure NBDE, a significant amount of decomposition was observed when it was exposed to air for 24 hours.

TABLE 1

Decomposition Tests of NBDE

| Example # | T (C.) | Reactive Gas | Stabilizer | Residue (g/L) |
|---|---|---|---|---|
| Comparative 1 | 80 | Air | None | >3.00 |
| Comparative 2 | 60 | Air | None | >3.00 |
| Comparative 3 | 80 | Air | 100 ppm MHQ | 0.61 |
| Comparative 4 | 80 | Air | 50 ppm MHQ | 2.21 |
| Comparative 5 | 80 | Air | 25 ppm MHQ | 2.63 |
| Comparative 6 | 60 | Air | 50 ppm MHQ | 0.27 |
| Comparative 7 | 60 | Air | 25 ppm MHQ | 1.15 |

When stabilized samples were exposed to air, less decomposition was observed in all cases compared to unstabilized samples. However, there is still room for improvement.

It is important to note that vaporizer means typically used in the semiconductor industry for chemical vapor deposition applications often use heat as one means of vaporization, but the amount of time that chemical resides in the vaporizer means is commonly less than one second. The tests performed above, with a 24 hour heating period, were designed to test the limits of the chemistry in the presence of a stabilizer. Further, the tests were designed to accelerate decomposition that might occur over much longer periods of time (e.g., one year) during shipping and storage of the chemical prior to use.

Though the data above suggest that higher concentrations of stabilizer are preferred, the actual concentration needed is a fine balance between appropriate stabilization of the chemical (where higher concentrations are preferred) and reduction of the amount of potential residue, such as the stabilizer itself, that could be left behind (where lower concentrations are preferred). The best balance between the two is met by stabilizing a cyclic alkene using 25 to 50 ppm of stabilizer such as MHQ, where the concentration is dependent on the type of stabilizer used.

Examples 1-4 and Comparative Examples 8-11

A second series of tests were devised to compare the decomposition of stabilized NBDE using different purge gases in the presence and absence of "adventitious air". In these tests, glass ampoules were filled with approximately 50 mL of NBDE stabilized with 50 ppm of MHQ, leaving approximately 15 mL of headspace. The samples were prepared in a nitrogen-purged glovebox to prevent exposure to adventitious gases before the experiment. The headspace of each container was then purged for 30 seconds with a purge gas using a tube that extended to the bottom of the container. The purge gas was bubbled through the sample at a rate where bubbles constantly rose through the liquid. Some samples then received approximately 2 mL of room air in the headspace of the container to approximate exposure to "adventitious air". All containers were sealed at ambient pressure.

Samples were then exposed to temperatures of 60 or 80° C. for a period of 24 hours to simulate accelerated decomposition conditions. After the experiment was complete, the volatiles in each ampoule were removed in vacuo at room temperature, and the non-volatile decomposition products remained behind. The extent of decomposition, or residue formation, was determined by comparing the mass of the container after the experiment to the mass of the container before the experiment. The difference between the two masses is the amount of decomposition that resulted in the sample under those conditions. The mass of the additive was subtracted out to give a result that only represents the decomposition that occurred, and the final mass was multiplied by 20 to give the amount of solid that would be found in 1 L of sample.

Results outlined in Table 2 show that for stabilized NBDE, more decomposition was observed for samples exposed to "adventitious air" for 24 hours than for samples that were purged and were free of "adventitious air".

Comparison of the data shows that samples purged with $CO_2$ experienced

TABLE 2

Decomposition Tests of Purged NBDE

| Example # | T (C.) | Purge Gas | Air Exposed | Stabilizer | Residue (g/L) |
|---|---|---|---|---|---|
| Example 1 | 80 | Nitrogen | No | 50 ppm MHQ | 0.14 |
| Comparative 8 | 80 | Nitrogen | Yes | 50 ppm MHQ | 1.94 |
| Example 2 | 60 | Nitrogen | No | 50 ppm MHQ | 0.01 |
| Comparative 9 | 60 | Nitrogen | Yes | 50 ppm MHQ | 0.35 |
| Example 3 | 80 | CO2 | No | 50 ppm MHQ | 0.11 |
| Comparative 10 | 80 | CO2 | Yes | 50 ppm MHQ | 0.76 |
| Example 4 | 60 | CO2 | No | 50 ppm MHQ | 0.00 |
| Comparative 11 | 60 | CO2 | Yes | 50 ppm MHQ | 0.39 | approximately the same or less decomposition than those exposed to nitrogen, whether air was present or absent. Additionally, less decomposition was experienced at a lower temperature (i.e., 60° C.) than at a higher one (i.e., 80° C.).

From this we can conclude that, containers initially handled under inert atmosphere, such as nitrogen, that are not purged (i.e., those most likely to contain "adventitious air") are likely to experience decomposition in spite of the fact that the cyclic alkene is stabilized. Containers purged with nitrogen to remove any adventitious air are likely to have less decomposition than containers that are not purged. Finally, purging with nitrogen is helpful, but purging with $CO_2$ can give an added desirable effect of reduced degradation, even in the presence of adventitious air.

Example 5

The precursor, NBDE, stabilized with 50 ppm of MHQ and purged with $CO_2$ is transferred, with the aid of helium pressure, from a stainless steel container through a chemical delivery line to a heated vaporizer at a flow rate of 1 mL/min. The precursor is vaporized into a chemical vapor process line that is heated to 80° C. and transported to a substrate using 500 sccm of carbon dioxide as a transport gas with the system base pressure held at 6 torr. During transport to the substrate, the precursor vapor and transport gas is mixed with a flow of methyldiethoxysilane (M-DEOS) in a proportion of approximately 60% M-DEOS and 40% NBDE. This gas mixture is exposed to a plasma power of 250 W. The substrate is heated to 150° C. with a substrate bias of −15 VDC. A carbon doped silicon oxide film is deposited on the substrate using these conditions.

Example 6

The precursor, NBDE, stabilized with 50 ppm of MHQ and purged with $CO_2$ is transferred, with the aid of helium pressure, from a stainless steel container through a chemical delivery line to a heated vaporizer at a flow rate of 1 mL/min. The precursor is vaporized into a chemical vapor process line that is heated to 80° C. and transported to a substrate using 500 sccm of carbon dioxide as a transport gas with the system base pressure held at 6 torr. During transport to the substrate, the precursor vapor and transport gas is mixed with a flow of TMCTS in a proportion of approximately 60% TMCTS and 40% NBDE. This gas mixture is exposed to a plasma power of 250 W. The substrate is heated to 150° C. with a substrate bias of −15 VDC. A carbon doped silicon oxide film is deposited on the substrate using these conditions.

Example 7

This example employs the process in Example 5, however the carbon doped silicon oxide film is treated by a post-deposition curing step. The film is annealed at 425° C. under nitrogen for 4 hours to remove substantially all of the NBDE porogen that remains in the film. This treatment typically gives a slightly thinner film with a lower dielectric constant.

Example 8

This example employs the process in Example 6, however the carbon doped silicon oxide film is treated by a post-deposition curing step. The film is annealed at 425° C. under nitrogen for 4 hours to remove substantially all of the NBDE porogen that remains in the film. This treatment typically gives a slightly thinner film with a lower dielectric constant.

Example 9

A stabilized cyclic alkene composition is prepared by adding 0.84 g MHQ to 16.8 kg of NBDE. The resulting mixture agitated until it becomes a homogeneous solution, and it is then packaged into a 5 gallon stainless steel container used for the semiconductor industry. Prior to sealing the container, the composition is purged by passing $CO_2$ into the container through the dip tube (i.e., tube extending to the bottom of the container through the liquid). The purge gas is bubbled through the composition, and the purge gas and other adventitious gases to be removed are expelled out of a vent at the top of the container at a rate of approximately 250 sccm for five minutes. Once the container is purged, it is sealed at ambient pressure. The resulting material in the purged container is used to make low k films according to the procedures described in examples 5, 6, 7 and 8.

Example 10

The purged stabilized alkene composition as described in Example 9 is made, except that the container is sealed under 5 psi of pressure. The resulting material in the purged container is used to make low k films according to the procedures described in examples 5, 6, 7 and 8.

Example 11

The purged stabilized alkene composition as described in Example 9 is made, except that the container is purged using CO instead of $CO_2$. The resulting material in the purged container is used to make low k films according to the procedures described in examples 5, 6, 7 and 8.

Example 12

The purged stabilized alkene composition as described in Example 11 is made, except that the container is sealed under 5 psi of pressure. The resulting material in the purged container is used to make low k films according to the procedures described in examples 5, 6, 7 and 8.

While we have shown and described several embodiments in accordance with our disclosure, it is to be clearly understood that the same are susceptible to numerous changes apparent to one skilled in the art. Therefore, we do not wish to be limited to the details shown and described but intend to show all changes and modifications which come within the scope of the appended claims.

The invention claimed is:

1. A stabilized cyclic alkene composition comprising:
one or more cyclic alkenes, and
at least one antioxidant compound of formula (I),

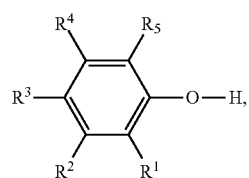

(I)

wherein $R_1$ through $R_5$ each independently is H, OH, $C_1$-$C_8$ linear, branched, or cyclic alkyl, $C_1$-$C_8$ linear, branched, or cyclic alkoxy or substituted or unsubstituted aryl; and
wherein said antioxidant compound is present in an amount between about 1 ppm and 200 ppm; and
wherein said composition is purged with at least one gas selected from the group consisting of: helium, neon, argon, krypton, xenon, radon, nitrogen, carbon monoxide and carbon dioxide, after said composition is introduced to a container intended for storage or shipping of said composition.

2. The composition of claim 1, wherein said gas is at least one gas selected from the group consisting of: helium, nitrogen, carbon monoxide and carbon dioxide.

3. The composition of claim 1, wherein said antioxidant compound is at least one compound selected form the group consisting of: phenol, 4-methylphenol, 3-methylphenol, 2-methylphenol, 4-ethylphenol, 4-propylphenol, 4-isopropylphenol, 4-butylphenol, 4-sec-butylphenol, 4-iso-butylphenol, 4-tertbutylphenol, 4-methoxyphenol, 3-methoxyphenol, 2-methoxyphenol, 4-ethoxyphenol, 2-(1-methylbutyl)phenol, 2-tert-butyl-6-methylphenol, 1,2-dihydroxybenzene, 2,4-di-tert-butylphenol, 2,6-di-tert-butyl-4-methylphenol (BHT), 1,3-dihydroxybenzene, hydroquinone, 3,4,5-trimethoxyphenol, 3-ethoxy-4-methylphenol, 4-propoxyphenol, 4-butoxyphenol, 2,4-dicyclohexyl-5-methylphenol, and 6-tert-butyl-1,2-dihydroxybenzene.

4. The composition of claim 3, wherein said antioxidant compound is at least one compound selected from the group consisting of: 4-methoxyphenol, 1,2-dihydroxybenzene, 6-tert-butyl-1,2-dihydroxybenzene, and 2,6-di-tert-butyl-4-methylphenol.

5. The composition of claim 1, wherein said antioxidant composition is present in an amount between about 1 ppm to about 100 ppm.

6. The composition of claim 1, wherein said antioxidant composition is present in an amount between about 100 ppm to 200 ppm.

7. The composition of claim 1, wherein said cyclic alkene has the general formula $C_nH_{2n-2x-y}R_y$, wherein n is an integer from 4 to 18, x is an integer wherein $1 \leq x \leq n/2$, y is an integer wherein $0 \leq y \leq 2n-2x$, and R is at least one component selected from the group consisting of: $C_1$-$C_{18}$ linear, branched, unsaturated, or cyclic alkyl, $C_1$-$C_{18}$ linear, branched, unsaturated, or cyclic alkoxy, substituted or unsubstituted aryl, or a substituted silicon containing substituent.

8. The composition of claim 1, wherein said cyclic alkene has the general formula $C_nH_{2n-(2x+2)-y}R_y$, wherein n is an integer from 5 to 18, x is an integer wherein $x \leq n/2$, y is an integer wherein $0 \leq Y \leq 2n-(2x+2)$, and R is at least one component selected from the group consisting of: $C_1$-$C_{18}$ linear, branched, unsaturated or cyclic alkyl, $C_1$-$C_{18}$ linear, branched, unsaturated or cyclic alkoxy, substituted or unsubstituted aryl, or a substituted silicon containing substituent.

9. The composition of claim 1, wherein said cyclic alkene has the general formula $C_nH_{2n-(2x+4)-y}R_y$, where n is an integer from 7 to 18, x is an integer wherein $x \leq n/2$, y is an integer wherein $0 \leq y \leq 2n-(2x+4)$, and R is at least one component selected from the group consisting of: $C_1$-$C_{18}$ linear, branched, unsaturated or cyclic alkyl, $C_1$-$C_{18}$ linear, branched, unsaturated or cyclic alkoxy, substituted or unsubstituted aryl, or a substituted silicon containing substituent.

10. The composition of claim 1, wherein said cyclic alkene is at least one compound selected from the group consisting of: dipentene, phellandrene, dicyclopentadiene, alpha-terpinene, gamma-terpinene, limonene, alpha-pinene, 3-carene, terpinolene, norbornene, norbornadiene, 5-vinyl-2-norbornene, and 5-ethylidene-2-norbornene.

11. The composition of claim 1, wherein said cyclic alkene is at least one compound selected from the group consisting of: dipentene, phellandrene, dicyclopentadiene, alpha-terpinene, gamma-terpinene, limonene, alpha-pinene, 3-carene, terpinolene, norbornene, norbornadiene, 5-vinyl-2norbornene, and 5-ethylidene-2-norbornene, and wherein said antioxidant compound is at least one compound selected from the group consisting of: 4-methoxyphenol, 1,2-dihydroxybenzene, 6-tert-butyl-1,2-dihydroxybenzene, and 2,6-di-tert-butyl-4-methylphenol.

12. A method for stabilizing a cyclic alkene, the method comprising adding at least one antioxidant compound of formula (I),

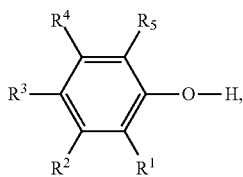

wherein $R_1$ through $R_5$ each independently is H, OH, $C_1$-$C_8$ linear, branched, or cyclic alkyl, $C_1$-$C_8$ linear, branched, or cyclic alkoxy or substituted or unsubstituted aryl to at least one cyclic alkene, wherein said antioxidant compound is present in an amount between about 1 ppm and 200 ppm, and purging said antioxidant compound and said cyclic alkene with at least one inert gas selected from the group consisting of: helium, neon, argon, krypton, xenon, radon, nitrogen, carbon monoxide and carbon dioxide, after said antioxidant compound and said cyclic alkene are introduced to a container intended for storage or shipping of said composition.

13. The method of claim 12, wherein said gas is at least one gas selected from the group consisting of helium, nitrogen, carbon monoxide and carbon dioxide.

14. The method of claim 12, wherein said antioxidant compound is at least one compound selected form the group consisting of: phenol, 4-methylphenol, 3-methylphenol, 2-methylphenol, 4-ethylphenol, 4-propylphenol, 4-isopropylphenol, 4-butylphenol, 4-sec-butylphenol, 4-iso-butylphenol, 4-tertbutylphenol, 4-methoxyphenol, 3-methoxyphenol, 2-methoxyphenol, 4-ethoxyphenol, 2-(1-methylbutyl)phenol, 2-tert-butyl-6-methylphenol, 1,2-dihydroxybenzene, 2,4-di-tert-butylphenol, 2,6-di-tert-butyl-4-methylphenol (BHT), 1,3-dihydroxybenzene, hydroquinone, 3,4,5-trimethoxyphenol, 3-ethoxy-4-methylphenol, 4-propoxyphenol, 4-butoxyphenol, 2,4-dicyclohexyl-5-methylphenol, and 6-tert-butyl-1,2-dihydroxybenzene.

15. The method of claim 14, wherein said antioxidant compound is at least one compound selected from the group consisting of: 4-methoxyphenol, 1,2-dihydroxybenzene, 6-tert-butyl-1,2-dihydroxybenzene, and 2,6-di-tert-butyl-4-methylphenol.

16. The method of claim 12, wherein said cyclic alkene has the general formula $C_nH_{2n-2x-y}R_y$, wherein n is an integer from 4 to 18, x is an integer wherein $1 \leq x \leq n/2$, y is an integer wherein $0 \leq Y \leq 2n-2x$, and R is at least one component selected from the group consisting of: $C_1$-$C_{18}$ linear, branched, unsaturated, or cyclic alkyl, $C_1$-$C_{18}$ linear, branched, unsaturated, or cyclic alkoxy, substituted or unsubstituted aryl, or a substituted silicon containing substituent.

17. The method of claim 12, wherein said cyclic alkene has the general formula $C_nH_{2n-(2x+2)-y}R_y$, wherein n is an integer from 5 to 18, x is an integer wherein $x \leq n/2$, y is an integer wherein $0 \leq Y \leq 2n-(2x+2)$, and R is at least one component selected from the group consisting of: $C_1$-$C_{18}$ linear, branched, unsaturated or cyclic alkyl, $C_1$-$C_{18}$ linear, branched, unsaturated or cyclic alkoxy, substituted or unsubstituted aryl, or a substituted silicon containing substituent.

18. The method of claim 12, wherein said cyclic alkene has the general formula $C_nH_{2n-(2x+4)-y}R_y$, where n is an integer from 7 to 18, x is an integer wherein $x \leq n/2$, y is an integer wherein $0 \leq Y \leq 2n-(2x+4)$, and R is at least one component selected from the group consisting of: $C_1$-$C_{18}$ linear, branched, unsaturated or cyclic alkyl, $C_1$-$C_{18}$ linear, branched, unsaturated or cyclic alkoxy, substituted or unsubstituted aryl, or a substituted silicon containing substituent.

19. The method of claim 12, wherein said cyclic alkene is at least one compound selected from the group consisting of: dipentene, phellandrene, dicyclopentadiene, alpha-terpinene, gamma-terpinene, limonene, alpha-pinene, 3-carene, terpinolene, norbornene, norbornadiene, 5-vinyl-2-norbornene, and 5-ethylidene-2-norbornene.

20. The method of claim 12, wherein said cyclic alkene is at least one compound selected from the group consisting of: dipentene, phellandrene, dicyclopentadiene, alpha-terpinene, gamma-terpinene, limonene, alpha-pinene, 3-carene, terpinolene, norbornene, norbornadiene, 5 vinyl-2-norbornene, and 5-ethylidene-2-norbornene, and wherein said antioxidant compound is at least one compound selected from the group consisting of 4-methoxyphenol, 1,2-dihydroxybenzene, 6-tert-butyl-1,2-dihydroxybenzene, and 2,6-di-tert-butyl-4-methylphenol.

21. A stabilized cyclic alkene composition consisting essentially of:
one or more cyclic alkenes, and
at least one antioxidant compound of formula (I),

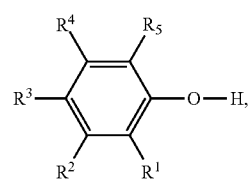

wherein $R_1$ through $R_5$ each independently is H, OH, $C_1$-$C_8$ linear, branched, or cyclic alkyl, $C_1$-$C_8$ linear, branched, or cyclic alkoxy or substituted or unsubstituted aryl; and at least one gas selected from the group consisting of: helium, nitrogen, carbon monoxide and carbon dioxide, and wherein said antioxidant compound is present in an amount between about 1 ppm and 200 ppm.

22. The composition of claim 21 wherein said gas is at least one gas selected from the group consisting of: nitrogen and carbon dioxide.

23. The composition of claim 21, wherein said antioxidant compound is at least one compound selected form the group consisting of phenol, 4-methylphenol, 3-methylphenol, 2-methylphenol, 4-ethylphenol, 4-propylphenol, 4-isopropylphenol, 4-butylphenol, 4-sec-butylphenol, 4-iso-butylphenol, 4-tertbutylphenol, 4-methoxyphenol, 3-methoxyphenol, 2-methoxyphenol, 4-ethoxyphenol, 2-(1-methylbutyl)phenol, 2-tert-butyl-6-methylphenol, 1,2-dihydroxybenzene, 2,4-di-tert-butylphenol, 2,6-di-tert-butyl-4-methylphenol (BHT), 1,3-dihydroxybenzene, hydroquinone, 3,4,5-trimethoxyphenol, 3-ethoxy-4-methylphenol, 4-propoxyphenol, 4-butoxyphenol, 2,4-dicyclohexyl-5-methylphenol, and 6-tert-butyl-1,2-dihydroxybenzene.

24. The composition of claim 23, wherein said antioxidant compound is at least one compound selected from the group consisting of: 4-methoxyphenol, 1,2-dihydroxybenzene, 6-tert-butyl-1,2-dihydroxybenzene, and 2,6-di-tert-butyl-4-methylphenol.

25. The composition of claim 21, wherein said antioxidant composition is present in an amount between about 1 ppm to about 100 ppm.

26. The composition of claim 21, wherein said antioxidant composition is present in an amount between about 100 ppm to 200 ppm.

27. The composition of claim 21, wherein said cyclic alkene has the general formula $C_nH_{2n-2x-y}R_y$, wherein n is an integer from 4 to 18, x is an integer wherein $1 \leq x \leq n/2$, y is an integer wherein $0 \leq y \leq 2n-2x$, and R is at least one component selected from the group consisting of $C_1$-$C_{18}$ linear, branched, unsaturated, or cyclic alkyl, $C_1$-$C_{18}$ linear, branched, unsaturated, or cyclic alkoxy, substituted or unsubstituted aryl, or a substituted silicon containing substituent.

28. The composition of claim 21, wherein said cyclic alkene has the general formula $C_nH_{2n-(2x+2)-y}R_y$, wherein n is an integer from 5 to 18, x is an integer wherein $x \leq n/2$, y is an integer wherein $0 \leq y \leq 2n-(2x+2)$, and R is at least one component selected from the group consisting of: $C_1$-$C_{18}$ linear, branched, unsaturated or cyclic alkyl, $C_1$-$C_{18}$ linear, branched, unsaturated or cyclic alkoxy, substituted or unsubstituted aryl, or a substituted silicon containing substituent.

29. The composition of claim 21, wherein said cyclic alkene has the general formula $C_nH_{2n-(2x+4)-y}R_y$, where n is an integer from 7 to 18, x is an integer wherein $x \leq n/2$, y is an integer wherein $0 \leq y \leq 2n-(2x+4)$, and R is at least one component selected from the group consisting of: $C_1$-$C_{18}$ linear, branched, unsaturated or cyclic alkyl, $C_1$-$C_{18}$ linear, branched, unsaturated or cyclic alkoxy, substituted or unsubstituted aryl, or a substituted silicon containing substituent.

30. A stabilized cyclic alkene composition comprising:
one or more cyclic alkenes, and
at least one antioxidant compound selected from the group consisting of 2-(benzyloxy)phenol, 4-benzyloxyphenol, 4-benzyl-2,6-di-tert-butylphenol, 2-(2-butenyl)phenol, 2-(4-methylbenzyl)phenol, and 2,4,6-tris-benzyloxyphenol,
wherein said composition is purged with at least one gas selected from the group consisting of: helium, neon, argon, krypton, xenon, radon, nitrogen, carbon monoxide and carbon dioxide, after said composition is introduced to a container intended for storage or shipping of said composition.

31. A method of forming a layer of carbon-doped silicon oxide on a substrate, the method comprising the steps of:
providing a cyclic alkene composition, a first silicon containing compound, and a substrate; and
forming the layer of the carbon-doped silicon oxide on the substrate, wherein said cyclic alkene composition comprises:
one or more cyclic alkenes; and
at least one antioxidant compound of Formula (I):

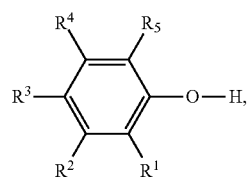

wherein $R_1$ through $R_5$ each independently is H, OH, $C_1$-$C_8$ linear, branched, or cyclic alkyl, $C_1$-$C_8$ linear, branched, or cyclic alkoxy or substituted or unsubstituted aryl, and
wherein said antioxidant compound is present in a concentration between 1 ppm and 200 ppm, and
wherein said cyclic alkene composition is purged with at least one gas selected from the group consisting of: helium, neon, argon, krypton, xenon, radon, nitrogen, carbon monoxide and carbon dioxide, after said cyclic alkene composition is introduced to a first container intended for storage or shipping of said composition.

32. The method of claim 31, further comprising the steps of:
providing said cyclic alkene composition in said first container, said first silicon containing compound in a second container, a film deposition tool, a film deposition chamber within said film deposition tool, and a stream of carrier gas to sweep said cyclic alkene composition and said first silicon containing compound through a connecting means into the film deposition chamber, wherein said substrate is disposed within said film deposition chamber of said film deposition tool;
connecting said first and second containers to said film deposition chamber within said film deposition tool;
introducing vapors of said cyclic alkene composition and said first silicon containing compound into said carrier gas stream; and
transporting said vapors of said cyclic alkene composition and said first silicon containing compound into said film deposition chamber.

33. The method of claim 31, wherein said cyclic alkene has the general formula $C_nH_{2n-2x-y}R_y$, wherein n is an integer from 4 to 18, x is an integer wherein $1 \leq x \leq n/2$, y is an integer wherein $0 \leq Y \leq 2n-2x$, and R is at least one component selected from the group consisting of: $C_1$-$C_{18}$ linear, branched, unsaturated, or cyclic alkyl, $C_1$-$C_{18}$ linear, branched, unsaturated, or cyclic alkoxy, substituted or unsubstituted aryl, or a substituted silicon containing substituent.

34. The method of claim 31, wherein said cyclic alkene has the general formula $C_nH_{2n-(2x+2)-y}R_y$, wherein n is an integer from 5 to 18, x is an integer wherein $x \leq n/2$, y is an integer wherein $0 \leq Y \leq 2n-(2x+2)$, and R is at least one component selected from the group consisting of: $C_1$-$C_{18}$ linear, branched, unsaturated or cyclic alkyl, $C_1$-$C_{18}$ linear, branched, unsaturated or cyclic alkoxy, substituted or unsubstituted aryl, or a substituted silicon containing substituent.

35. The method of claim 31, wherein said cyclic alkene has the general formula $C_nH_{2n-(2x+4)-y}R_y$, where n is an integer from 7 to 18, x is an integer wherein $x \leq n/2$, y is an integer wherein $0 \leq Y \leq 2n-(2x+4)$, and R is at least one component selected from the group consisting of: $C_1$-$C_{18}$ linear, branched, unsaturated or cyclic alkyl, $C_1$-$C_{18}$ linear, branched, unsaturated or cyclic alkoxy, substituted or unsubstituted aryl, or a substituted silicon containing substituent.

36. The method of claim 31, wherein said cyclic alkene is at least one compound selected from the group consisting of: dipentene, phellandrene, dicyclopentadiene, alpha-terpinene, gamma-terpinene, limonene, alpha-pinene, 3-carene, terpinolene, norbornene, norbornadiene, 5-vinyl-2-norbornene, and 5-ethylidene-2-norbornene.

37. The method of claim 31, wherein said antioxidant compound is at least one compound selected form the group consisting of: phenol, 4-methylphenol, 3-methylphenol, 2-methylphenol, 4-ethylphenol, 4-propylphenol, 4-isopropylphenol, 4-butylphenol, 4-sec-butylphenol, 4-iso-butylphenol, 4-tertbutylphenol, 4-methoxyphenol, 3-methoxyphenol, 2-methoxyphenol, 4-ethoxyphenol, 2-(1-methylbutyl)phenol, 2-tert-butyl-6-methylphenol, 1,2-dihydroxybenzene, 2,4-di-tert-butylphenol, 2,6-di-tert-butyl-4-methylphenol (BHT), 1,3-dihydroxybenzene, hydroquinone, 3,4,5-trimethoxyphenol, 3-ethoxy-4-methylphenol, 4-propoxyphenol, 4-butoxyphenol, 2,4-dicyclohexyl-5-methylphenol, and 6-tert-butyl-1,2-dihydroxybenzene.

38. The method of claim 37, wherein said antioxidant compound is at least one compound selected from the group consisting of: 4-methoxyphenol, 1,2-dihydroxybenzene, 6-tert-butyl-1,2-dihydroxybenzene, and 2,6-di-tert-butyl-4-methylphenol.

39. The method of claim 31, wherein said cyclic alkene is at least one compound selected from the group consisting of: dipentene, phellandrene, dicyclopentadiene, alpha-terpinene, gamma-terpinene, limonene, alpha-pinene, 3-carene, terpinolene, norbornene, norbornadiene, 5-vinyl-2norbornene, and 5-ethylidene-2-norbornene, and wherein said antioxidant compound is at least one compound selected from the group consisting of: 4-methoxyphenol, 1,2-dihydroxybenzene, 6-tert-butyl-1,2-dihydroxybenzene, and 2,6-di-tert-butyl-4-methylphenol.

40. The method of claim 31, further comprising providing a second silicon containing compound different from the first silicon containing compound.

* * * * *

UNITED STATES PATENT AND TRADEMARK OFFICE
CERTIFICATE OF CORRECTION

PATENT NO. : 7,883,639 B2
APPLICATION NO. : 11/519524
DATED : February 8, 2011
INVENTOR(S) : Daniel J. Teff and John L. Chagolla It is certified that error appears in the above-identified patent and that said Letters Patent is hereby corrected as shown below:

IN THE CLAIMS:

Column 23, Line 45

In Claim 1, delete " 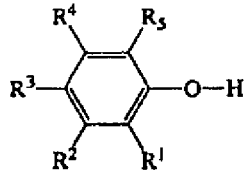 " and insert -- 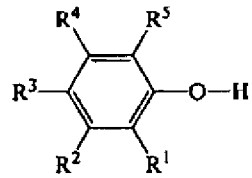 -- therefor.

Column 23, Line 50
In Claim 1, delete "$R_1$ through $R_5$" and insert -- $R^1$ through $R^5$ -- therefor.

Column 23, Line 65
In Claim 3, delete "form" and insert -- from -- therefor.

Column 24, Line 59-60
In Claim 11 delete "2norbornene, --," and insert -- 2-norbornene, -- therefor.

Column 25, Line 5

In Claim 12, delete " 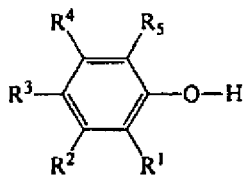 " and insert -- 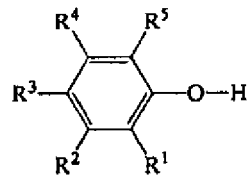 -- therefor.

Column 25, Line 12
In Claim 12, delete "$R_1$ through $R_5$" and insert -- $R^1$ through $R^5$ -- therefor.

Column 25, Line 29
In Claim 14 delete "form" and insert -- from -- therefor.

Signed and Sealed this
Twenty-eighth Day of February, 2012

David J. Kappos
*Director of the United States Patent and Trademark Office*

CERTIFICATE OF CORRECTION (continued)

Column 26, Line 13
In Claim 20 delete "5 vinyl-2-norbornene," and insert -- 5-vinyl-2-norbornene, -- therefore.

Column 26, Line 30

In Claim 21, delete " 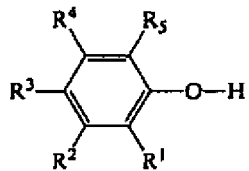 " and insert -- 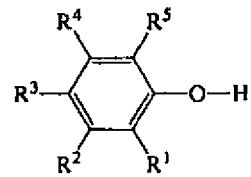 -- therefor.

Column 26, Line 34
In Claim 21, delete "$R_1$ through $R_5$" and insert -- $R^1$ through $R^5$ -- therefor.

Column 26, Line 45
In Claim 23, delete "form" and insert -- from -- therefor

Column 27, Line 55

In Claim 31, delete " 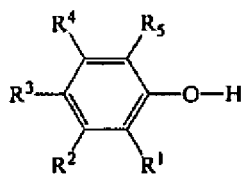 " and insert -- 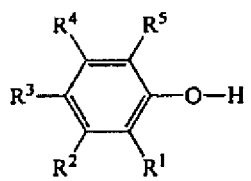 -- therefor.

Column 27, Line 59
In Claim 31, delete "$R_1$ through $R_5$" and insert -- $R^1$ through $R^5$ -- therefor.

Column 28, Line 54
In Claim 37, delete "form" and insert -- from -- therefor.

Column 29, Line 8
In Claim 39, delete "2norbornene," and insert -- 2-norbornene, -- therefor.